(12) United States Patent
Baker et al.

(10) Patent No.: US 9,795,775 B2
(45) Date of Patent: Oct. 24, 2017

(54) MICRONEEDLES WITH IMPROVED OPEN CHANNEL CROSS-SECTIONAL GEOMETRIES

(71) Applicant: Kimberly-Clark Worldwide, Inc., Neenah, WI (US)

(72) Inventors: Andrew Baker, Norcross, GA (US); Russell F. Ross, Atlanta, GA (US); Sridhar Ranganathan, Suwanee, GA (US)

(73) Assignee: KIMBERLY-CLARK WORLDWIDE, INC., Neenah, WI (US)

( * ) Notice: Subject to any disclaimer, the term of this patent is extended or adjusted under 35 U.S.C. 154(b) by 0 days.

(21) Appl. No.: 14/787,044

(22) PCT Filed: May 20, 2014

(86) PCT No.: PCT/IB2014/061564
§ 371 (c)(1),
(2) Date: Oct. 26, 2015

(87) PCT Pub. No.: WO2014/188343
PCT Pub. Date: Nov. 27, 2014

(65) Prior Publication Data
US 2016/0106965 A1 Apr. 21, 2016

Related U.S. Application Data

(60) Provisional application No. 61/826,755, filed on May 23, 2013.

(51) Int. Cl.
*A61M 5/00* (2006.01)
*A61M 37/00* (2006.01)

(52) U.S. Cl.
CPC ... *A61M 37/0015* (2013.01); *A61M 2037/003* (2013.01); *A61M 2037/0023* (2013.01); *A61M 2037/0038* (2013.01)

(58) Field of Classification Search
CPC .... A61M 2037/0023; A61M 2037/003; A61M 2037/0038; A61M 37/0015
(Continued)

(56) References Cited

U.S. PATENT DOCUMENTS

| 5,527,288 A | 6/1996 | Gross et al. |
| 5,928,207 A | 7/1999 | Pisano et al. |

(Continued)

FOREIGN PATENT DOCUMENTS

| KR | 2007/0060609 | 6/2007 |
| WO | WO 03/045837 | 6/2003 |

(Continued)

OTHER PUBLICATIONS

L.A. Romero and F.G. Yost Article "Flow in an Open Channel Capillary" Sandia National Laboratories, Albuquerque, NM 87185-5800, USA Jan. 20, 1995 and revised in Mar. 19, 1996. vol. 322. (21 pages).

(Continued)

*Primary Examiner* — Phillip Gray
(74) *Attorney, Agent, or Firm* — Dority & Manning, P.A.

(57) ABSTRACT

In one aspect a drug delivery device may include a reservoir containing a liquid drug formulation and a microneedle assembly in fluid communication with the reservoir. The microneedle assembly may include a plurality of microneedles, with each microneedle defining an open channel for receiving a drug formulation. The open channel may have a normalized hydraulic radius ranging from about 0.1 to about 0.8. The open channel may also have a liquid-to-solid interfacial energy and a liquid-to-vapor interfacial energy when a fixed volume of the drug formulation is received therein. In addition, the drug formulation and a cross-sectional geometry of the open channel may be selected and configured such that the liquid-to-solid energy exceeds the liquid-to-vapor energy as the length of the fixed volume of drug formulation is increased within the open channel.

30 Claims, 10 Drawing Sheets

(58) Field of Classification Search
USPC .................................................. 604/173, 117
See application file for complete search history.

(56) References Cited

U.S. PATENT DOCUMENTS

| | | |
|---|---|---|
| 5,972,505 A | 10/1999 | Phillips et al. |
| 6,171,446 B1 | 1/2001 | Diaz-Kotti |
| 6,611,707 B1 | 8/2003 | Prausnitz et al. |
| 2002/0045859 A1* | 4/2002 | Gartstein ........... A45D 26/0004 604/117 |
| 2005/0171480 A1 | 8/2005 | Mukerjee et al. |
| 2006/0202385 A1 | 9/2006 | Xu et al. |
| 2012/0238841 A1 | 9/2012 | Castle et al. |

FOREIGN PATENT DOCUMENTS

| | | |
|---|---|---|
| WO | WO 2004/072105 | 8/2004 |
| WO | WO 2008/140049 | 11/2008 |
| WO | WO 2010/059605 | 5/2010 |
| WO | WO 2011/021996 | 2/2011 |
| WO | WO 2011/144591 | 11/2011 |
| WO | WO 2013/061208 | 5/2013 |

OTHER PUBLICATIONS

PCT International Search Report and Written Opinion PCT/IB2014/061564, International Filing Date of May 20, 2014. (12 pages).

* cited by examiner

MICRONEEDLES WITH IMPROVED OPEN CHANNEL CROSS-SECTIONAL GEOMETRIES

FIELD OF THE INVENTION

The present subject matter relates generally to the delivery of drug formulations using drug delivery devices and, more particularly, to microneedles for a drug delivery device having open channels that provide for enhanced wicking of a drug formulation within the microneedles.

BACKGROUND OF THE INVENTION

The delivery of drugs to a patient is conventionally performed in a variety of different ways. For example, intravenous delivery is by injection directly into a blood vessel; intraperitoneal delivery is by injection into the peritoneum; subcutaneous delivery is under the skin; intramuscular delivery is into a muscle; and oral delivery is through the mouth. A common method for drug delivery, and for collection of body fluids, is through the skin. Skin is composed of the epidermis, including the stratum corneum, the stratum granulosum, the stratum spinosum, and the stratum basale, and the dermis, containing, among other things, the capillary layer. The stratum corneum is a tough, scaly layer made of dead cell tissue that extends around 10-20 microns from the skin surface and has no blood supply. Because of the density of this layer of cells, moving compounds across the skin, either into or out of the body, can be very difficult.

Current techniques for delivering local pharmaceuticals through the skin include methods that use needles or other skin piercing devices and methods that do not use such devices. Those methods that do not use needles typically involve: (a) topical applications, (b) iontophoresis, (c) electroporation, (d) laser perforation or alteration, (e) carriers or vehicles, which are compounds that modify the chemical properties of either the stratum corneum and/or the pharmaceutical, (f) physical pretreatment of the skin, such as abrasion of the stratum corneum (e.g., repeatedly applying and removing adhesive tape), and (g) sonophoresis, which involves modifying the barrier function of stratum corneum by ultrasound. Invasive procedures, such as use of needles or lances, can effectively overcome the barrier function of the stratum corneum. However, these methods suffer from several major disadvantages, including pain, local skin damage, bleeding and risk of infection at the injection site. These methods also usually require a trained administrator and are not well-suited for repeated, long-term use. Additionally, drug delivery through the skin has been relatively imprecise in both location and dosage of the pharmaceutical. Some of the problems include movement of the patient during administration, delivery of incomplete dosages, difficulties in administering more than one pharmaceutical at the same time, controlling the rate of delivery and difficulties in delivering a pharmaceutical to the appropriate part of the skin. Drugs have traditionally been diluted to enable handling of the proper dosages. This dilution step can cause storage as well as delivery problems. Thus, it would be advantageous to be able to use small, precise volumes of pharmaceuticals for delivery into and/or through the skin.

Microneedles have been proposed as an alternate method of delivering drugs through the skin. The microneedles typically have a hollow shaft, similar to larger conventional medical needles, so that drug formulations may be delivered through the hollow shaft. Various active mechanisms (e.g., pumps, springs and/or other pressuring mechanism) have been employed to initiate the flow of the drug formulation through such devices. U.S. Pat. No. 6,611,707 to Prausnitz et al. and U.S. Pat. No. 5,527,288 to Gross et al., for example, describe devices that each include a drug reservoir positioned over a housing that includes an array of hollow microneedles. A drug formulation is delivered from the reservoir by applying a force against the drug itself or against the reservoir, such as by pressing against the top of a flexible reservoir bag, to cause the formulation to flow out through the microneedles. Unfortunately, the flow rate of the drug formulation injected into the skin using such force is often far greater than the absorption rate of the skin itself. As a result, all or a significant portion of the drug formulation will often flow upwards at the interface between the skin and the microneedles to the surface of the skin.

As such, a need currently exists for a drug delivery device that can easily and effectively deliver a drug formulation in a manner to improve the controlled delivery and bioavailability of the drug.

BRIEF DESCRIPTION OF THE INVENTION

Aspects and advantages of the invention will be set forth in part in the following description, or may be obvious from the description, or may be learned through practice of the invention.

In one aspect, the present subject matter is directed to a drug delivery device. The device may include a reservoir containing a liquid drug formulation and a microneedle assembly in fluid communication with the reservoir. The microneedle assembly may include a support defining an upper surface and a lower surface and a plurality of microneedles extending from the lower surface. Each microneedle may define an open channel for receiving a drug formulation. The open channel may have a normalized hydraulic radius ranging from about 0.1 to about 0.8 and, in further aspects, from about 0.1 to about 0.5. The open channel may also have a liquid-to-solid interfacial energy and a liquid-to-vapor interfacial energy when a fixed volume of the drug formulation is received therein. In addition, the drug formulation and a cross-sectional geometry of the open channel may be selected and configured such that the liquid-to-solid energy exceeds the liquid-to-vapor energy as the length of the fixed volume of drug formulation is increased within the open channel.

In another aspect, the present subject matter is directed to a drug delivery device. The device may include a reservoir configured to initially retain a drug formulation and a microneedle assembly in fluid communication with the reservoir. The microneedle assembly may be configured such that a passive fluid flow of the drug formulation is directed through the microneedle assembly. The microneedle assembly may include a support defining an upper surface and a lower surface and a plurality of microneedles extending from the lower surface. Each microneedle may define an open channel for receiving the drug formulation. The open channel may have a normalized hydraulic radius ranging from 0.1 to 0.8 or, in a further aspect, from 0.1 to 0.5. The open channel may also have a liquid-to-solid interfacial energy and a liquid-to-vapor interfacial energy when a fixed volume of the drug formulation is received therein. In addition, the drug formulation and a cross-sectional geometry of the open channel may be selected and configured such that the liquid-to-solid interfacial energy exceeds the liquid-to-vapor interfacial energy as the length of the fixed volume of drug formulation is increased within the open channel.

In a further aspect, the present subject matter is directed to a drug delivery device. The device may include a reservoir containing a liquid drug formulation and a microneedle assembly in fluid communication with the reservoir. The microneedle assembly may include a support defining an upper surface and a lower surface and a plurality of microneedles extending from the lower surface. Each microneedle may define an open channel for receiving a drug formulation and may have a skin contact area ranging from about 1,500 um² to about 262,500 um². The open channel may also have a liquid-to-solid interfacial energy and a liquid-to-vapor interfacial energy when a fixed volume of the drug formulation is received therein. In addition, the drug formulation and a cross-sectional geometry of the open channel may be selected and configured such that the liquid-to-solid energy exceeds the liquid-to-vapor energy as a length of the fixed volume of drug formulation is increased within the open channel.

In yet another aspect, the present subject matter is directed to a drug delivery device. The device may include a reservoir containing a liquid drug formulation and a microneedle assembly in fluid communication with the reservoir. The microneedle assembly may include a support defining an upper surface and a lower surface and a plurality of microneedles extending from the lower surface. Each microneedle may define an open channel for receiving a drug formulation. The open channel may have a liquid-to-solid interfacial energy and a liquid-to-vapor interfacial energy when a fixed volume of the drug formulation is received therein. In addition, the drug formulation and a cross-sectional geometry of the open channel may be selected and configured such that the following constraint is satisfied:

$$\frac{d}{dL}[E_{LV} + E_{LS}]_V < 0$$

wherein, $E_{LV}$ corresponds to the liquid-to-vapor interfacial energy, $E_{LS}$ corresponds to the liquid-to-solid interfacial energy, L corresponds to the length of the drug formulation and V corresponds to the fixed volume of the drug formulation.

In an even further aspect, the present subject matter is directed to a drug delivery device having any combination of components and/or features described herein.

These and other features, aspects and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which.

DETAILED DESCRIPTION OF THE INVENTION

Figure 1:
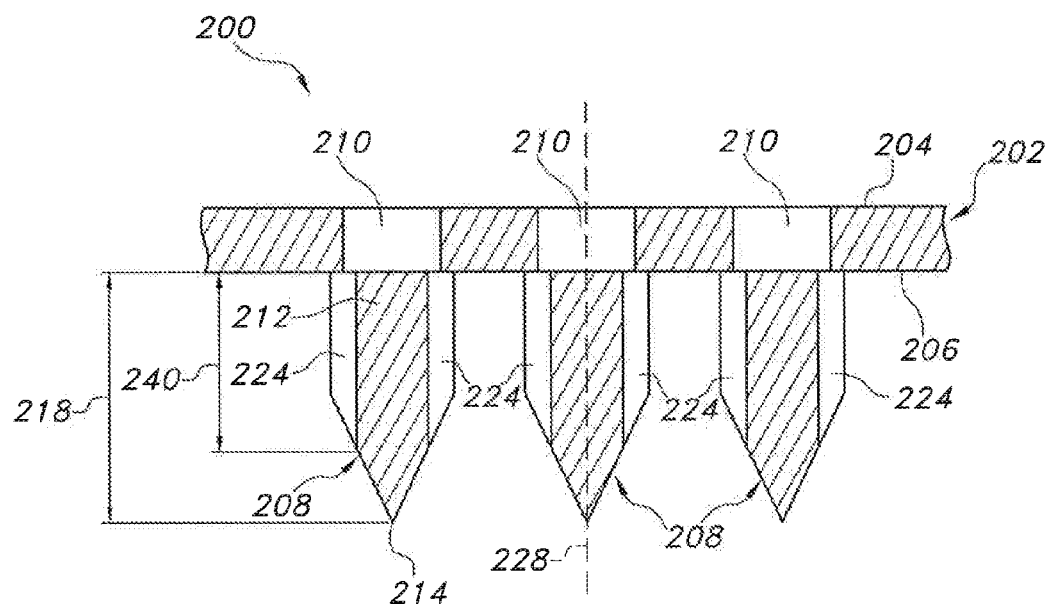
FIG. 1 illustrates a partial, cross-sectional view of one embodiment of a microneedle assembly in accordance with aspects of the present subject matter.

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield a still further embodiment. Thus, it is intended that the present invention covers such modifications and variations as come within the scope of the appended claims and their equivalents.

In general, the present subject matter is directed to microneedles for a drug delivery device having open channels with improved cross-sectional geometries. Specifically, in several embodiments, the cross-sectional geometry of each channel may be selected such that the sum of the capillary forces along the wetted perimeter of the channel exceeds the total surface tension forces on the exposed fluid surfaces within such channel for all levels of a fluid drug formulation within the channel, thereby allowing the drug to be wicked along the entire length of each channel. As will be described below, to achieve the desired flow of a drug formulation within a channel, the relationship between the cross-sectional geometry of the channel and the contact angle defined between the channel and the drug formulation must be balanced in a manner that allows the channel to be substantially self-draining (i.e., so that a fluid would spread indefinitely along the surface of the channel) while maintaining the cross-sectional area of the channel at a level that ensures unimpeded flow of the drug formulation into and through the channel.

It should be appreciated that, in several embodiments of the present subject matter, the disclosed drug delivery device may be configured as a transdermal drug delivery device and, thus, may be designed to deliver a drug formulation(s) into but not through a user's skin (i.e., to a location between the stratum corneum and the inner surface of the epidermis). However, in other embodiments, the drug delivery device may be configured to deliver a drug formulation completely through the user's skin.

It should also be appreciated that, in several embodiments, the disclosed drug delivery device may be configured as a passive drug delivery device. As such, unlike active devices that rely on pressurizing or otherwise forcing a drug formulation through the microneedles, the passive device may rely on a capillary driven flow of the drug through the microneedles and into and/or through the skin. Specifically, the passive device may use the relative surface tension of the drug and the surface energy of the microneedle material to cause drug movement through the microneedles. In addition, the negative pressure generated due to skin absorption may also serve to draw the drug from the reservoir through the microneedles. When designing a passive drug delivery device, it is desirable to have a complete wicking of the drug formulation within the microneedle channels so that the drug effectively drains along the full length of each microneedle. As will be described below, the cross-sectional geometry of the microneedle channels may be selected in combination with the actual drug formulation being delivered via the device to achieve the desired draining characteristics.

Figure 2:
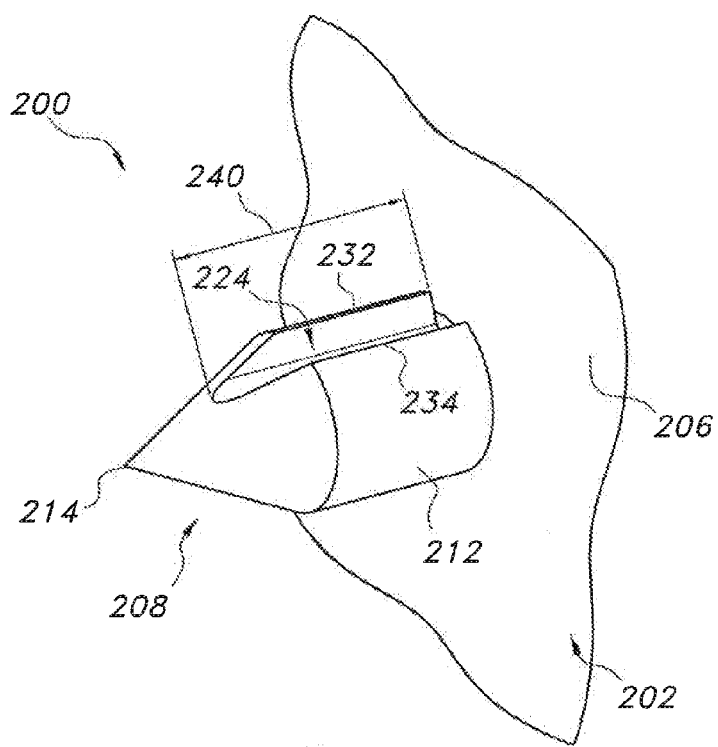
FIG. 2 illustrates a perspective view of one of the microneedles of the microneedle assembly shown in FIG. 1.
Figure 3:
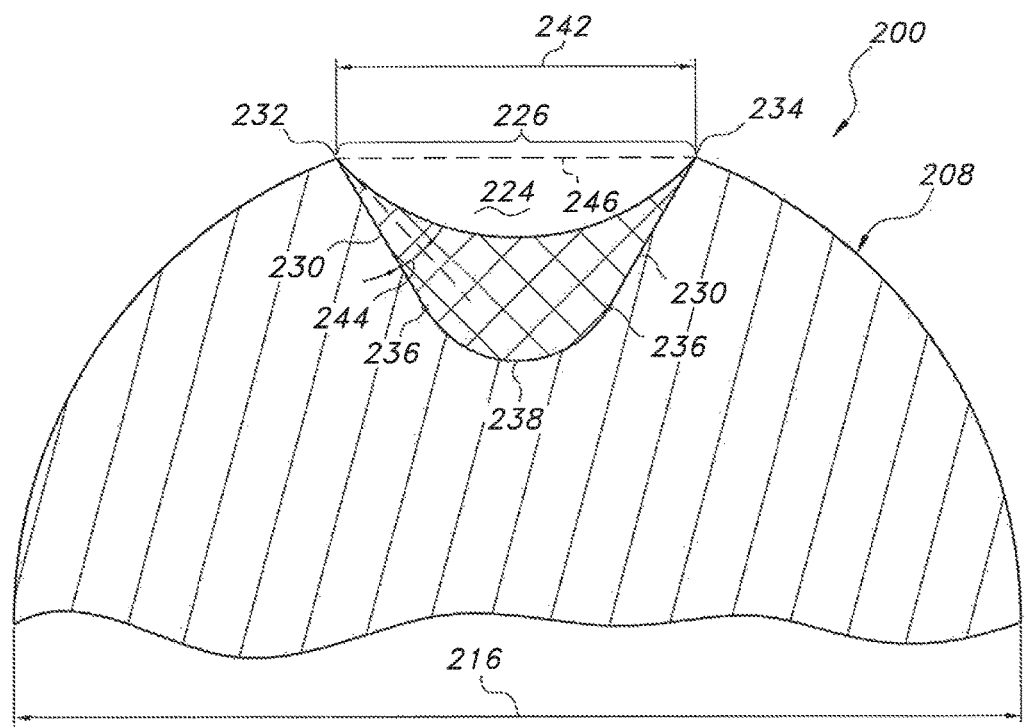
FIG. 3 illustrates a partial, cross-sectional view of the microneedle shown in FIG. 2, particularly illustrating the microneedle with a channel defining a rounded-bottom "V" shaped cross-section.

Referring now to the drawings, FIGS. 1-3 illustrate partial views of one embodiment of a microneedle assembly 200 in accordance with aspects of the present subject matter. In particular, FIG. 1 illustrates a partial, cross-sectional view of the microneedle assembly 200. Additionally, FIG. 2 illustrates a perspective view of one of the microneedles of the assembly 200 shown in FIG. 1 and FIG. 3 illustrates a partial, cross-sectional view of the microneedle shown in FIG. 2.

In general, the microneedle assembly 200 may have any suitable configuration known in the art for delivering a fluidic drug formulation (often referred to herein as simply a "fluid") into and/or through a user's skin. In several embodiments, the microneedle assembly 200 may include a plurality of skin penetrating members (i.e., microneedles) extending outwardly from a suitable substrate or support. For example, as particularly shown in FIG. 1, the microneedle assembly 200 includes a support 202 defining a top surface 204 and a bottom surface 206 and an array of microneedles 208 extending outwardly from the bottom surface 206. The support 202 may generally be constructed from a rigid, semi-rigid or flexible sheet of material, such as a metal material, a ceramic material, a plastic material and/or any other suitable material. In addition, the support 202 may define one or more apertures between its top and bottom surfaces 204, 206 to permit fluids to flow therebetween. For example, as shown in FIG. 1, a single aperture 210 may be defined in the support 202 at the location of each microneedle 208 to permit fluids to be delivered from the top surface 204 to such microneedle 208. However, in other embodiments, the support 202 may define any other suitable number of apertures 210 positioned at and/or spaced apart from the location of each microneedle 208.

Additionally, as shown in FIGS. 1 and 2, each microneedle 208 may generally be configured to define a piercing or needle-like shape (e.g., a conical or pyramidal shape or a cylindrical shape transitioning to a conical or pyramidal shape) extending between a base 212 positioned adjacent to and/or extending from the bottom surface 206 of the support 202 and a tip 214 disposed opposite the base 212. As is generally understood, the tip 214 may correspond to the point of each microneedle 208 that is disposed furthest away from the support 202 and may define the smallest diameter of each microneedle 208. In several embodiments, an average diameter 216 (FIG. 3) of each microneedle 208 may range from about 50 micrometers (um) to about 250 um, such as from about 60 um to about 200 um or from about 80 um to about 120 um and any other subranges therebetween.

Moreover, each microneedle 208 may generally define any suitable length 218 between its base 212 and its tip 214 that is sufficient to allow the microneedles 208 to penetrate the stratum corneum and pass into and/or through the epidermis. For example, in one embodiment, each microneedle 208 may define a length 218 of less than about 2000 micrometers (um), such as less than about 1750 um, or less than about 1500 um, or less than about 1250 um and any other subranges therebetween. However, in certain embodiments, it may be desirable to limit the length 218 of the microneedles 208 such that they do not penetrate through the inner surface of the epidermis and into the dermis; such embodiments advantageously help minimize pain for the patient receiving the drug formulation. For example, in one embodiment, each microneedle 208 may define a length 218 of less than about 1000 micrometers (um), such as a length ranging from about 900 um to about 100 um or from about 700 um to about 150 um or from about 500 urn to about 175 um or from about 400 um to about 200 um and any other subranges therebetween.

It should be appreciated that the length 218 of the microneedles 208 may vary depending on the location at which the microneedle assembly 200 is actually being used on a user. For example, the length of the microneedles 208 for an assembly 200 to be used on a user's leg may differ substantially from the length of the microneedles 208 for an assembly 200 to be used on a user's arm.

It should also be appreciated that FIG. 1 only illustrates a portion of a suitable microneedle assembly 200 and, thus, the microneedle assembly 200 may generally include any number of microneedles 208 extending from its support 202.

Figure 10:
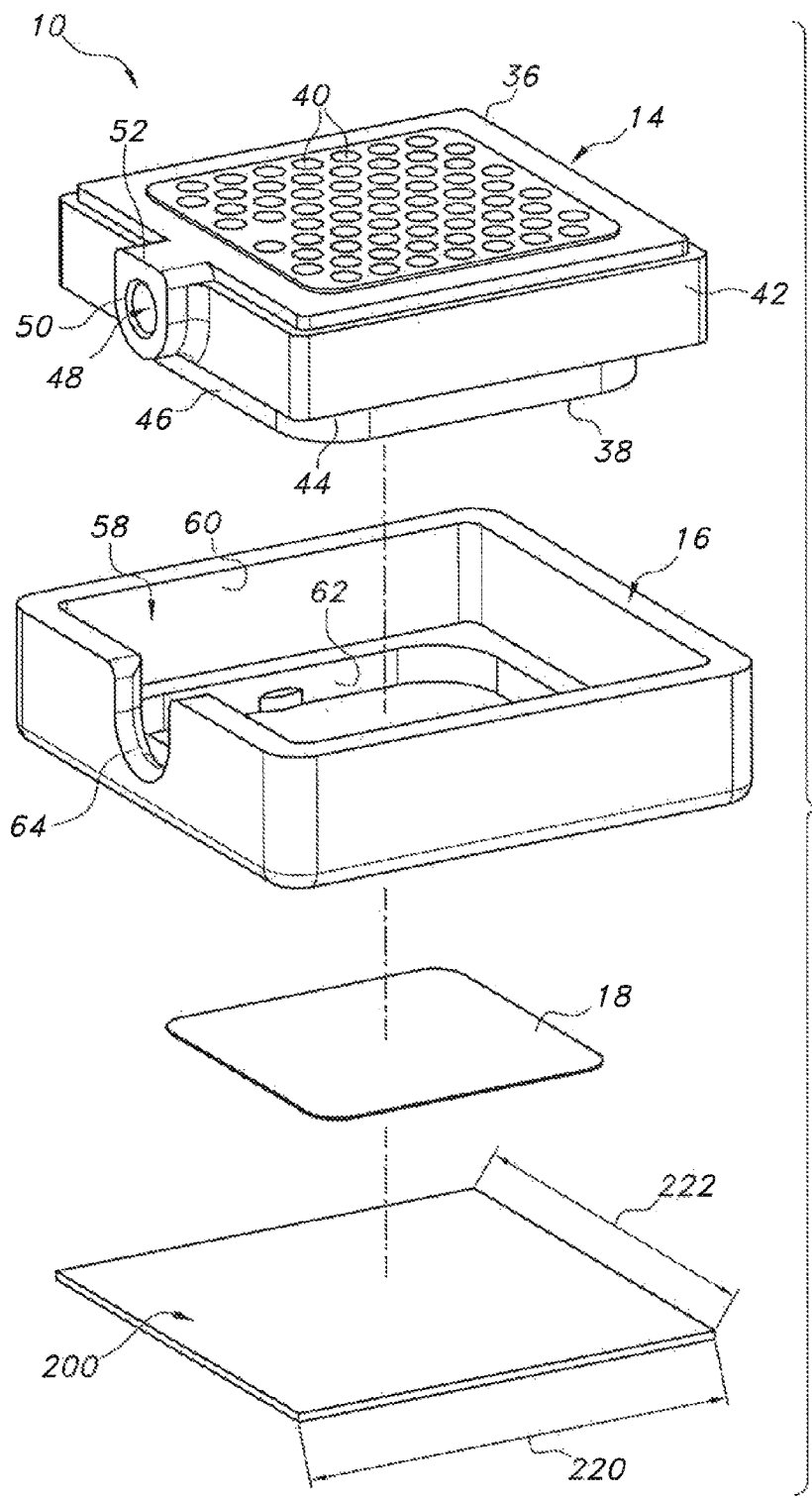
FIG. 10 illustrates an exploded, perspective view of various components that may be included within one embodiment of a passive drug delivery device in accordance with aspects of the present subject matter.

For example, in one embodiment, the actual number of microneedles 208 included within the microneedle assembly 200 may range from about 10 microneedles per square centimeter (cm$^2$) to about 1,500 microneedles per cm$^2$, such as from about 50 microneedles per cm$^2$, to about 1250 microneedles per cm$^2$ or from about 100 microneedles per cm$^2$ to about 500 microneedles per cm$^2$ and any other subranges therebetween. In addition, the actual dimensions of the microneedle assembly 200, itself, may generally vary depending on the configuration of the drug delivery device within which it is being used. However, the total array of microneedles may generally define a width 220 (FIG. 10) and a length 222 (FIG. 10). In one embodiment, the width 220 may range from about 5,000 micrometers (um) to about 25,000 um, such as from about 8,000 um to about 15,000 um or from about 9,000 um to about 11,000 um. Similarly, in one embodiment, the length 222 may range from about 5,000 micrometers (um) to about 25,000 um, such as from about 8,000 um to about 15,000 um or from about 9,000 um to about 11,000 urn.

Additionally, it should be appreciated that the microneedles 208 may generally be arranged on the support 202 in a variety of different patterns, and such patterns may be designed for any particular use. For example, in one embodiment, the microneedles 208 may be spaced apart in a uniform manner, such as in a rectangular or square grid or in concentric circles. In such an embodiment, the spacing of the microneedles 208 may generally depend on numerous factors, including, but not limited to, the length 218 and diameter 216 of the microneedles 208, as well as the amount and type of drug formulation that is intended to be delivered through the microneedles 208.

Moreover, each microneedle 208 may define one or more open channels 224 in fluid communication with the apertures 210 defined the support 202. As used herein, the term "open channel" refers to a channel 224 defined around the outer perimeter of a microneedle 208 such that the channel 224 is open to the outside environment along at least a portion of its length. For example, as shown in the illustrated embodiment, each microneedle includes a pair of open channels 224 defined along its outer perimeter such that each channel 224 is exposed to the outside environment along its open side (indicated by the bracket 226 in FIG. 3). In other embodiments, each microneedle 208 may include any other number of open channels 224 defined around its outer perimeter, such as a single open channel 224 or three or more open channels 224. Additionally, in one embodiment, each channel 224 may be configured to extend lengthwise generally parallel to a longitudinal axis 228 of its corresponding microneedle 208. However, in other embodiments, the channels 224 may have an angled orientation relative to the longitudinal axis 228. In a further embodiment (not shown), the channel(s) 224 may be exposed on the outer surface of each microneedle 208 some distance below the bottom surface 206 of the support 202. Regardless, each channel 224 may generally be configured to form a pathway that enables a drug formulation to flow from the top surface 204 of the support 202, through the apertures 210 and into the channels 224, at which point the drug formulation may be delivered into and/or through the user's skin.

It should be appreciated that each channel 224 may be configured to define any suitable cross-sectional shape capable of providing the disclosed device with the ability to drain a drug formulation along the full length of the channel 224. For example, as particularly shown in FIG. 3, each channel 224 defines a substantially parabolic or rounded-bottom "V" shaped cross-section. As described herein, a round-bottom "V" shaped or parabolic cross-section is generally characterized by substantially straight sidewalls 230 extending from each outer edge of the channel 224 (e.g., a first outer edge 232 and a second outer edge 234) to transition points 236 and a curved or rounded bottom wall 238 extending between the transition points 236. In certain embodiments, a parabolic shaped channel desirably forms a narrower groove such that the distance from the vertex to the focal point is less than half of the channel depth (i.e., distance from the vertex or bottom of the channel 224 to the reference 224 extending between the outer edges 232, 234 of the channel 224). However, in other embodiments, the channels 224 may be configured to define any other suitable cross-sectional shape, such as those having a substantially rectangular or trapezoidal shape. As will be described below, depending on the cross-sectional shape of the channels 224, the geometry of each channel 224 may be selected in combination with the drug formulation to obtain the high draining channel functionality required by passive fluid flow drug devices.

As shown in FIGS. 1 and 2, each channel 224 may define a length 240 extending at least partially between the bottom surface 206 of the support 202 and the tip 214 of the microneedle 208. In general, the length 240 of the channels 224 may vary depending on the overall length 218 of the microneedles 208 as well as the desired depth to which the drug formulation is to be delivered into and/or through the user's skin. However, in several embodiments, the length 240 of each channel 224 may generally range from about 100 micrometers (um) to about 2000 um, such as from about 150 um to about 1600 um or from about 200 um to about 500 um and any other subranges therebetween. In a further aspect, the length of the channels 224 may be between about 100% and about 10% of the length of the microneedle 208, and in still further embodiments, the length of the channels 224 may be between about 80% and about 15% or even between about 50% and about 20% of the length of the microneedle 208. Further, in certain embodiments, it may be desirable for the majority of the channel 224 to be located on the distal half of the microneedle 208 (i.e. on the half located away from the support 202). Additionally, as particularly shown in FIG. 3, each channel 224 may also define an open width 242 corresponding to the width of the channel 224 along its open side 226 (i.e., the width defined between the outer edges 232, 234 of the channel 224). In several embodiments, the open width 242 may range from about 15 micrometers (um) to about 175 um, such as from about 20 um to about 100 um or from about 25 um to about 50 um and any other subranges therebetween. Moreover, in several embodiments, the open width 242 may correspond to the maximum width of each channel 224 and the width of the channel 224 at its innermost point (i.e., at the bottom of the channel) may be equal to, for instance, less than 50% of the open width 242.

Moreover, each channel 224 may also have a skin contact area that is generally a function of its length 240 and open width 242. Specifically, the skin contract area may be the total area defined between the outer edges 232, 234 of each channel along its entire length 240. As such, the skin contact area may generally correspond to the area of drug formulation within the channel 224 that can be exposed to a patient's skin. In several embodiments, the skin contact area per channel 224 may range from about 1,500 micrometers squared (um$^2$) to about 100,000 um$^2$, such as from about 3,000 um$^2$ to about 50,000 um$^2$ or from about 5,000 um$^2$ to about 20,000 um$^2$ and any other subranges therebetween.

As indicated above, in several embodiments, the cross-sectional geometry of the channels 224 and the drug formulation, itself, are mutually selected in order to provide a drug delivery device in which spontaneous or self-draining capillary flow through each channel 224 will occur one the microneedles 208 are inserted inside a body. As is generally understood, the capillary-driven flow rate of fluid through an open channel 224 is influenced primarily by two factors, the capillary forces within the channel 224 and the hydraulic radius of the channel 224. The capillary forces are generally a function of the shape of the channel 224, itself, together with the contact angle of the fluid at the interface defined between the fluid and the channel 224 (i.e., angle 244 in FIG. 3) and the surface energy of the fluid. In particular, the capillary pressure is inversely proportional to a cross-sectional dimension of the channel 224 (e.g., radius, width, area, etc.) and directly proportional to the surface energy of the subject fluid, multiplied by the cosine of the contact angle 244. As a result, channels 224 with smaller dimensions, sharper angles and/or lower contact angles 244 result in higher capillary forces that act to pull fluid through the channels 224.

In contrast, the hydraulic radius is related to the resistance to move fluid within/through an open channel 224, with the flow resistance increasing as the hydraulic radius is decreased. In general, the hydraulic radius is a function of the cross-sectional area of a channel 224 together with its wetted perimeter, as represented below in the following equation (Equation 1):

$$R_h = \frac{A}{P_w} \quad (1)$$

wherein, $R_h$ corresponds to the hydraulic radius of the channel 224, A corresponds to the cross-sectional area of the channel 224 and $P_w$ corresponds to the wetted perimeter of the channel 224. Such parameters may be identified, for example, for the channel 224 shown in FIG. 3. Specifically, the cross-sectional area corresponds to the area defined between the walls 230, 238 of the channel 224 and the reference line 246 extending between the outer edges 232, 234 of the channel 224. In addition, the wetted perimeter corresponds to the perimeter of the cross-sectional area of the channel 224 that is in direct contact with fluid. For example, in the embodiment shown in FIG. 3, the wetted perimeter correspond to the perimeter extending along the walls 230, 238 of the channel 224 from the first outer edge 232 to the second outer edge 234.

The hydraulic radius of an open channel 224 increases as its cross-sectional shape is made more circular. Thus, prior focus has often been on increasing the channel volume or decreasing the flow resistance within the channels 224, in such case each channel 224 may be designed to a have semi-circular cross-sectional shape. However, as indicated above, it is desirable to have a self-draining capillary-driven flow through the channels 224, which may be achieved, at least in part, by configuring the channels 224 to have smaller dimensions and sharper angles. Thus, in order to enhance the self-draining characteristics of the channels 224 while maintaining their cross-sectional dimensions at a level that ensures unimpeded flow of fluid into and through the channels 224, the geometrical configuration of each channel 224 must be carefully selected in a manner that balances both the hydraulic radius and the capillary forces within the channel 224.

In order to assess the specific cross-sectional geometry of a channel 224 independent of its scale, the hydraulic radius may be normalized by scaling the geometry to fit within a unit circle (i.e., a circle with a radius of one). Thereafter, the relevant dimensional parameters associated with the specific cross-sectional shape of the channel 224 may be analyzed (together with the design constraints associated with its draining characteristics) to determine one or more values for a normalized hydraulic radius that allows for unimpeded flow through the channels 224 while still providing the desired self-draining characteristics. For example, by analyzing various cross-sectional geometries for the channels 224 in combination with liquid formulations, the inventors of the present subject matter have determined that a channel 224 having a normalized hydraulic radius that is greater than 0.1 and less than 0.8 desirably exhibits both reduced flow resistance and enhanced draining characteristics for passive drug delivery devices.

Figure 4:
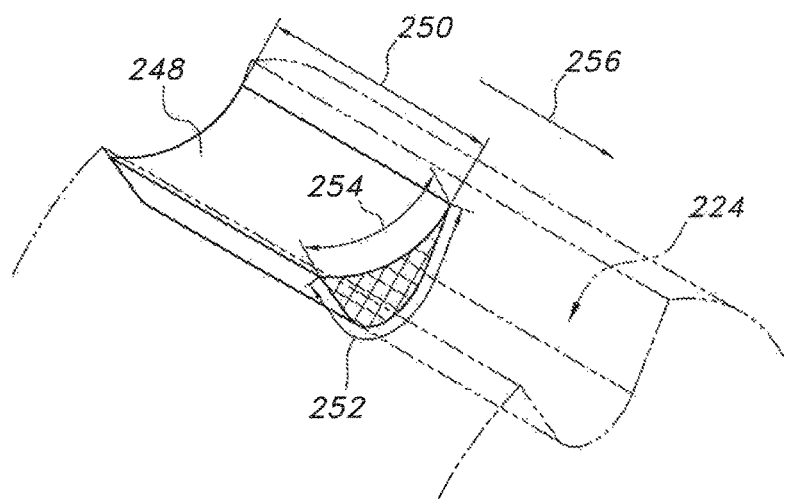
FIG. 4 illustrates a partial, perspective view of a fixed volume of a fluid, such as a drug formulation, contained within a microneedle channel, with the channel being shown in phantom lines.

Additionally, to assess the self-draining characteristics of a drug delivery device configured to deliver a particular drug formulation and having microneedles 208 defining a specific cross-sectional channel shape, the surface energy of the fluid within the channel 224 and its interaction with the channel 224 may be analyzed to determine the change in such energy with spreading of the fluid along the length of the channel 224. For example, FIG. 4 illustrates a perspective view of an open channel 224 (shown in phantom lines) with fluid 248 contained therein having a fixed volume and defining a fluid length 250. The total surface energy of the fluid 248 within the channel 224 is generally equal to the sum of a liquid-to-solid interfacial energy and a liquid-to-vapor interfacial energy. The liquid-to-solid interfacial energy may generally be a function of a liquid/solid interface length 252 defined at the interface between the channel 224 and fluid 248 and generally corresponding to the wetted perimeter of the channel 224 at the leading edge of the fluid 248. Similarly, the liquid-to-vapor interfacial energy may generally be a function of a liquid/vapor length 254 defined along the interface between the fluid 248 and the surrounding environment at the leading edge of the fluid 248 (e.g., the arc length of the top surface of the fluid 248 at its leading edge). Formulaic representations of what are believed to be critical components to achieving the desired spontaneous channel filling functionality are provided below in the following equations (Equations 2 and 3):

$$E_{LS} = -L * L_g * \gamma * \cos(\theta) \quad (2)$$

$$E_{LV} = L * L_S * \gamma \quad (3)$$

wherein, $E_{LS}$ corresponds to the liquid-to-solid interfacial energy, $E_{LV}$ corresponds to the liquid-to-vapor interfacial energy, L corresponds to the fluid length 250 of the fluid 248 within the channel 224, $L_g$ corresponds to the liquid/solid interface length 252, $\gamma$ corresponds to the liquid surface tension, $\theta$ corresponds to the contact angle 244 (FIG. 3) defined between the fluid 248 and the channel 224 and $L_S$ corresponds to the liquid/vapor length interface 254.

To provide a self-draining channel 224, the liquid-to-solid interfacial energy must exceed liquid-to-vapor interfacial energy, thereby pulling the fluid downward towards the bottom of the channel 224 as the fluid flows along the length of the channel 224 (i.e., in the direction of arrow 256 (FIG. 4)). Specifically, the properties of the drug formulation, together with the cross-sectional geometry of the channel 224, must be configured such that the liquid-to-solid interfacial energy exceeds the liquid-to-vapor interfacial energy as the fluid length 250 is increased within the open channel 224. In other words, for a fixed volume of fluid 248 within an open channel 224, the channel may be self-draining if the change in the difference between the liquid-to-vapor interfacial energy and the liquid-to-solid interfacial energy with changes in the fluid length 250 is less than zero. Such a relationship may be expressed by the following equation (Equation 4):

$$\frac{d}{dL}[(E_{LV} + E_{LS})]_V = \frac{d}{dL}[L*\gamma*(L_s - L_g*\cos(\theta))]_V < 0 \quad (4)$$

wherein, $E_{LV}$ corresponds to the liquid-to-vapor interfacial energy, $E_{LS}$ corresponds to the liquid-to-solid interfacial energy, L corresponds to the fluid length 250, γ corresponds to the liquid surface tension, $L_S$ corresponds to the liquid/vapor interface length 254, $L_g$ corresponds to the liquid/solid interface length 252, θ corresponds to the contact angle 244 (FIG. 3) and V corresponds to the fixed volume of the fluid 248.

Figure 5:
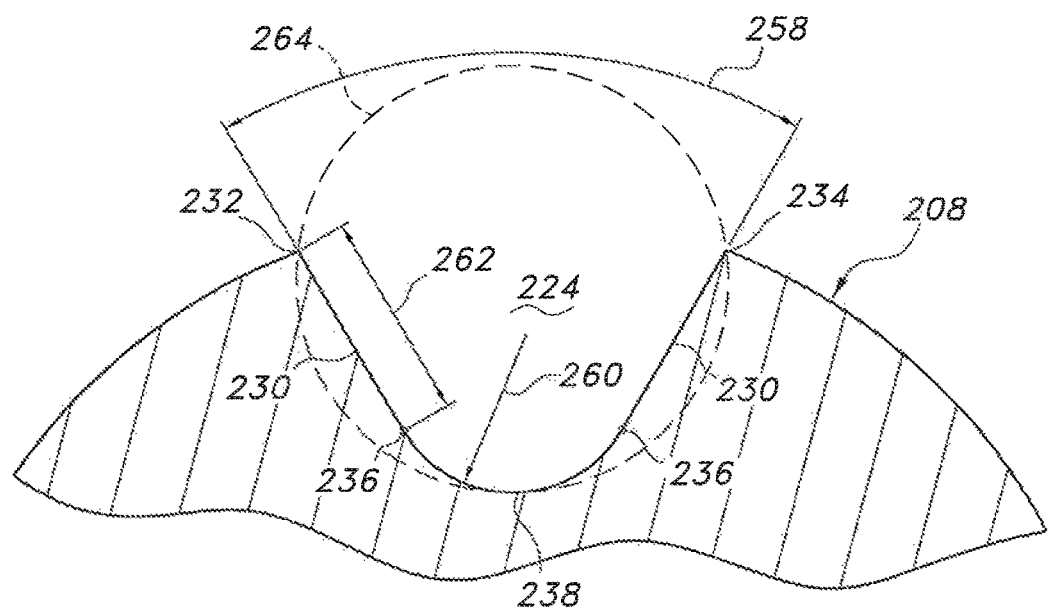
FIG. 5 illustrates a partial, cross-sectional view of a microneedle having a channel defining a rounded-bottom "V" shaped cross-section in accordance with aspects of the present subject matter, particularly illustrating the channel scaled to fit within a unit circle.

The composition of the elements of the disclosed device and certain types channel structures can be selected to achieve the relationships described herein and provide a drug delivery device having the desired spontaneous drainage within its microneedle channels. For example, FIG. 5 illustrates a partial cross-sectional view of a microneedle 208 including a parabolic or rounded-bottom "V" shaped channel 224. As shown, the cross-sectional geometry of the channel 224 may generally be defined by a groove angle 258 (i.e., the angle defined between the sidewalls 230 of the channel 224), a base radius 250 (i.e., the radius of curvature at the rounded-off apex or bottom wall 236 of the channel 224) and a side length 262 (i.e., the length of each sidewall 230 define between from the channel's outer edges 232, 234 and its transition points 236). As represented below in the following equations (i.e., Equations 5-7), Equation 4 may be modified in light of the dimensional parameters associated with parabolic or rounded-bottom "V" shaped channels 224 to characterize the relationship between such dimensional parameters and the contact angle defined between the channels 224 and the drug formulation:

$$\theta > \frac{\pi}{2} - \varphi \quad (5)$$

$$\frac{\pi}{4} - \frac{\varphi}{2} \le \theta \le \frac{\pi}{2} - \varphi \quad (6)$$

$$\theta < \frac{\pi}{4} - \frac{\varphi}{2} \quad (7)$$

wherein, θ corresponds to the contact angle 244 (FIG. 3) defined between the fluid and the channel 224 and 2*φ corresponds to the groove angle 258 of the channel 224.

Each of the above equations (i.e., Equations 5-7) provides a design constraint for defining the channel structure and drug composition needed to achieve desired draining characteristics for the channel 224. Specifically, if Equation 5 is satisfied, the fluid will not adequately drain within the channel 224. However, if Equation 6 is satisfied, the channel 224 will partially drain fluid (i.e., spontaneously pull fluid from the reservoir into the channel). For example, the fluid may drain downward into the channel 224 along a substantial portion of its side length 262 (i.e., to a location between the outer edges 232, 234 and the transition points 236). Additionally, if Equation 7 is satisfied, the channel 224 will be completely self-draining and the fluid will drain downwards along the entire and/or substantially the entire length of the channel 224 into the rounded bottom of the channel 224 beyond the transition points 236. In other words, fluid will spontaneously wick the full length of the channel 224 regardless of its length when the channel 224 has a geometrical configuration satisfying Equation 7.

As indicated above, by taking into consideration the design constraints related to the draining characteristics of a channel 224, the dimensional parameters associated with such channel 224 may also be analyzed to determine one or more suitable values for its normalized hydraulic radius. For example, as shown in FIG. 5, the channel 224 has been scaled to fit within a unit circle 264, thereby allowing a normalized hydraulic radius to be calculated for the channel 224. In general, for the parabolic or rounded-bottom "V" shaped channel 224 shown in FIG. 5, the normalized hydraulic radius is a function of both the groove angle 258 and the ratio between the base radius 260 and the side length 262 of the channel 224. Thus, by analyzing such dimensional parameters, a normalized hydraulic radius may be determined for the channel 224 that also satisfies the relevant design constraints for the desired draining characteristics. For example, a set of curves may be generated that shows the relationship between the normalized hydraulic radius, the groove angle 258 and the ratio between the base radius 260 and the side length 262.

In performing such an analysis, it has been determined by the inventors of the present subject matter that a normalized hydraulic radius ranging from 0.1 to 0.8 (e.g., including any suitable subranges therebetween, such as a range from 0.1 to 0.4 or range 0.4 to 0.8 or a range from 0.3 to 0.5) will provide a sufficiently reduced flow resistance within the channel 224 when taking into account the additionally relevant design constraints for the channel's draining characteristics. Thus, in several embodiments, a suitable geometry for a parabolic or rounded-bottom "V" shaped channel 224 is one that has a normalized hydraulic radius ranging from 0.1 to 0.8 and that satisfies either Equation 6 (i.e., to provide an partially self-draining channel) or Equation 7 (i.e., to provide a fully self-draining channel).

Figure 6:
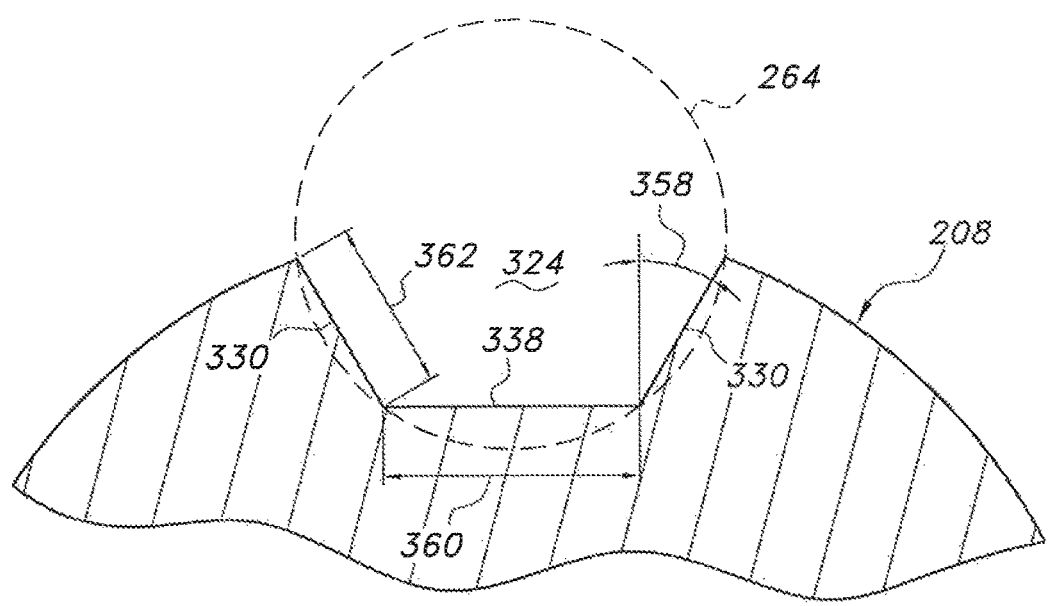
FIG. 6 illustrates a partial, cross-sectional view of a microneedle having a channel defining a trapezoidal shaped cross-section in accordance with aspects of the present subject matter, particularly illustrating the channel scaled to fit within a unit circle.

It should be appreciated that the required interactions and relationships may also be defined for other suitable cross-sectional channel shapes. For example, FIG. 6 illustrates a partial cross-sectional view of a microneedle 208 include a channel 324 having a straight-edged trapezoidal cross-sectional shape. Similar to the channel 224 described above, the channel 324 may be scaled to fit within a unit circle 264 to allow a normalized hydraulic radius to be calculated for the channel 324. As shown, the cross-sectional geometry of the channel 324 may generally be defined by a groove angle 358 (i.e., the angle defined by each sidewall 330 of the channel 324), a base width 360 (i.e., the width defined by a bottom wall 338 of the channel 324) and a side length 362 (i.e., the length of each sidewall 330 extending from the channel's outer edge to its bottom wall 338). As indicated above, the design constraint on the normalized hydraulic radius may be same for all cross-sectional shapes. Thus, for the illustrated trapezoidal shaped channel 324, a preferred geometry for the channel 324 has a normalized hydraulic radius ranging from 0.1 to 0.8. However, given its different cross-sectional shape, the overall device design incorporating a trapezoidal shaped channel will differ in various respects from that described above with reference to the parabolic or rounded-bottom "V" shaped channel 224. Specifically, by considering the relevant design and functional criteria discussed herein for a trapezoidal shaped channel 324, the self-draining characteristics of the channel 324 may be characterized as falling into three distinct categories, represented below in the following equations (i.e., Equations 8-10):

$$\varphi > \frac{\pi}{2} - \theta \quad (8)$$

$$\frac{\pi}{2} - 2.3*\theta \leq \varphi \leq \frac{\pi}{2} - \theta \quad (9)$$

$$\varphi < \frac{\pi}{2} - 2.3*\theta \quad (10)$$

wherein, θ corresponds to the contact angle 244 (FIG. 3) defined between the fluid and the channel 324 and 2*ϕ corresponds to the groove angle 358 of the channel 324.

Similar to Equations 5-7, each of the above equations (i.e., Equations 8-10) provides a design constraint for defining the structure and composition necessary to achieve the desired draining characteristics of the channel 324. Specifically, if Equation 8 is satisfied, the fluid will not adequately drain within the channel 324. However, if Equation 9 is satisfied, the channel 324 will partially drain fluid (i.e. spontaneously pull fluid from the reservoir into the channel). For example, the fluid may drain downward into the channel 324 along a substantial portion of its side length 362. Additionally, if Equation 10 is satisfied, the channel 324 will be completely self-draining and the fluid will drain downwards along the entire and/or substantially the entire length of the channel 324. For example, fluid will drain downward and contact the bottom wall 338 when the channel 324 has a geometrical configuration satisfying Equation 10. Thus, in several embodiments, a suitable geometry for a trapezoidal shaped channel 324 (considering the properties of the drug formulation being delivered through the channel 324) is one that has a normalized hydraulic radius ranging from 0.1 to 0.8 and that satisfies either Equation 9 (i.e., to provide an partially self-draining channel) or Equation 10 (i.e., to provide a fully self-draining channel).

Figure 7:
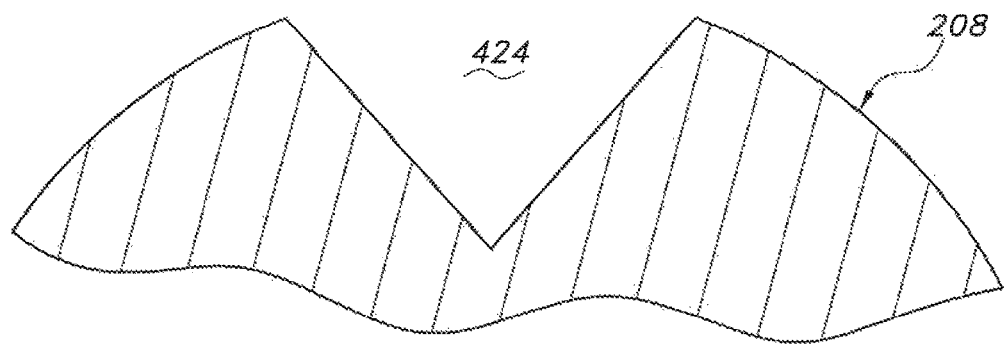
FIG. 7 illustrates a partial, cross-sectional view of a microneedle having a channel defining a straight "V" shaped cross-section in accordance with aspects of the present subject matter.
Figure 8:
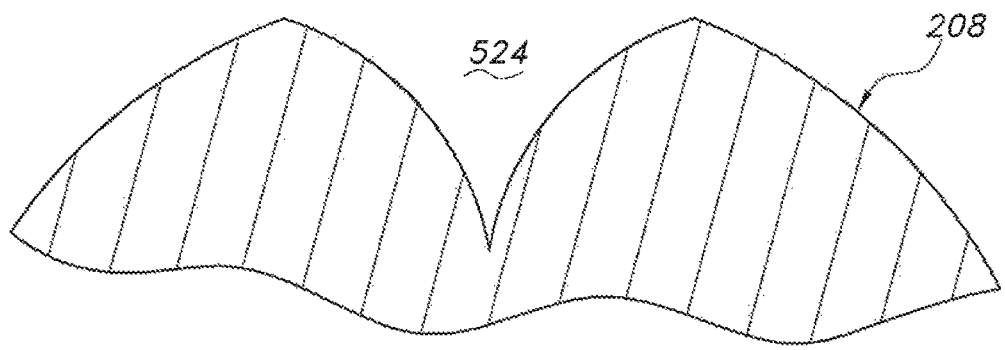
FIG. 8 illustrates a partial, cross-sectional view of a microneedle having a channel defining a "V" shaped cross-section with continuously curved sidewalls in accordance with aspects of the present subject matter.

In other embodiments, such an analysis may be performed on any other cross-sectional channel shape to define the required interactions and relationships for achieving, the desired flow through a microneedle channel. For instance, other suitable cross-sectional shapes may include a "V" shaped cross-section including straight sidewalls terminating at a sharp corner at the bottom of the channel (e.g., the channel 424 shown in FIG. 7), a "V" shaped cross-section have continuously curved convex or concave sidewalls (e.g., the channel 524 shown in FIG. 8) or an inverted, rounded trapezoidal cross-sectional shape (e.g., the channel 624 shown in FIG. 9 having rounded edges at its bottom).

Figure 11:
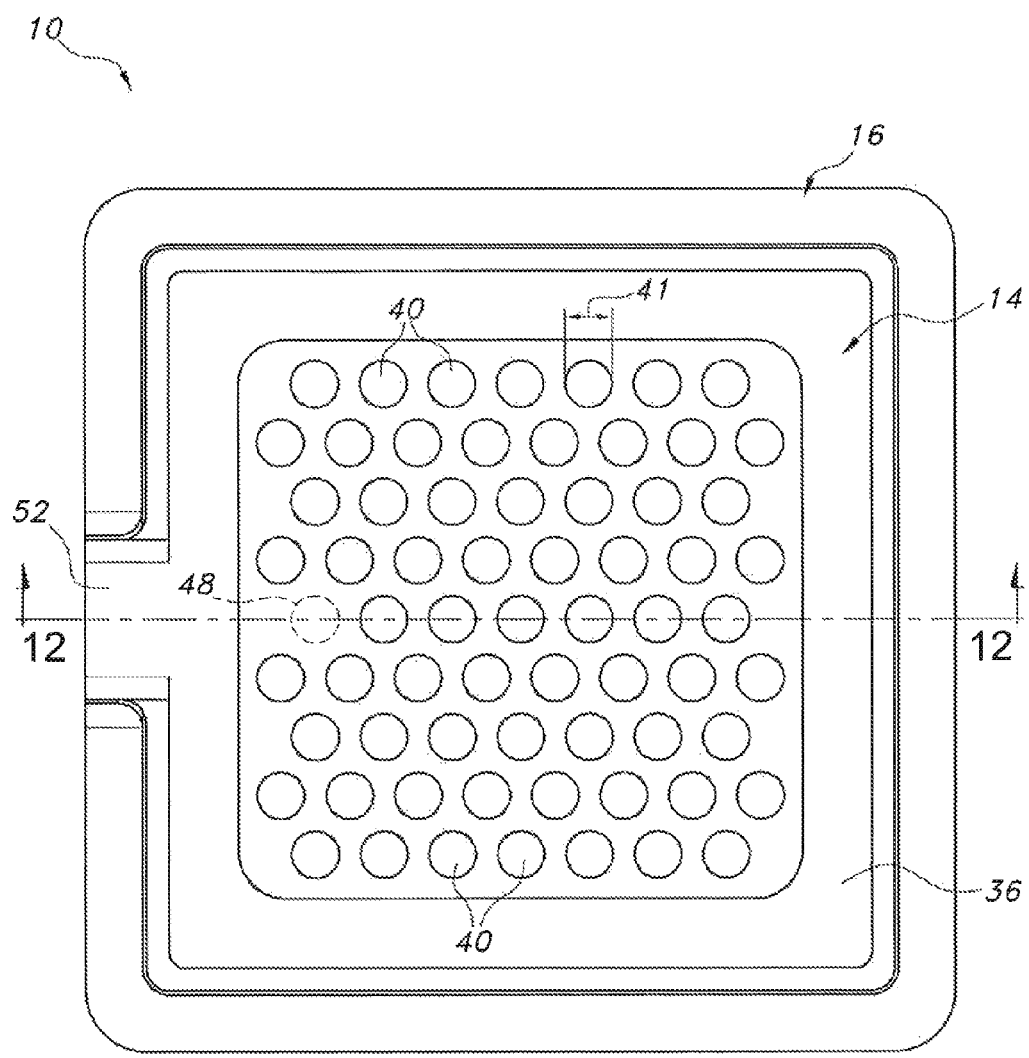
FIG. 11 illustrates a top, assembled view of the device components shown in FIG. 10.
Figure 12:
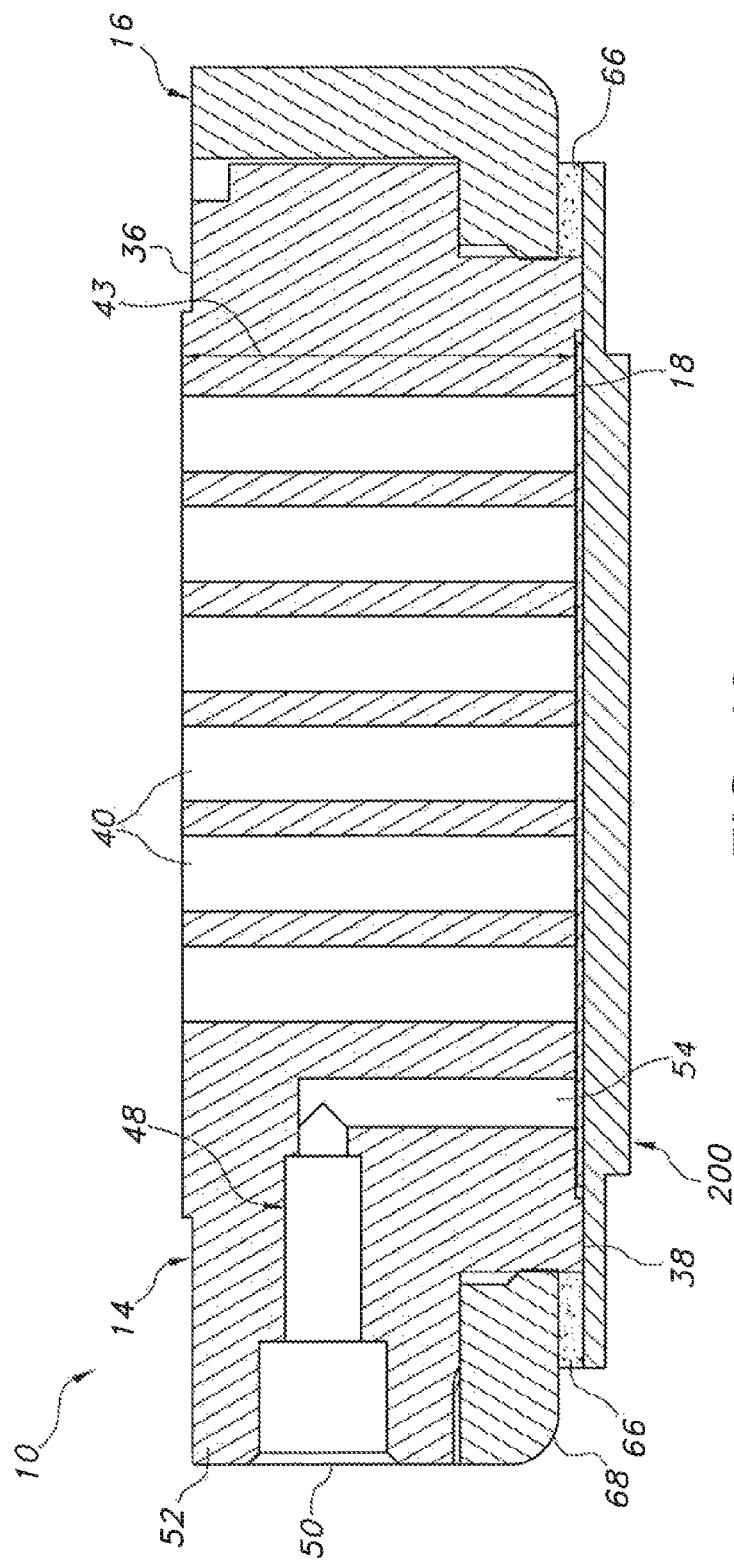
FIG. 12 illustrates a cross-sectional view of the device components shown in FIG. 11 taken about line 12-12.

Referring now to FIGS. 10-12, several views of various components that may form all or part of one embodiment of a passive drug delivery device 10 are illustrated in accordance with aspects of the present subject matter. It should be appreciated that the illustrated device 10 is simply illustrated to provide one example of a suitable passive drug delivery device with which the disclosed microneedle assembly 200 may be advantageously used. Thus, one of ordinary skill in the art should readily appreciate that the present subject matter need not be limited to any specific type of passive drug delivery device and that the microneedle assembly 200 described above may be utilized with any suitable device configuration.

As shown, the device 10 may include a skin penetrating assembly (e.g., microneedle assembly 200) for delivering a fluidic drug formulation into and/or through the skin of a user of the device 10, a reservoir 14 for initially retaining the drug formulation, a reservoir frame 16 configured to receive and/or support at least a portion of the reservoir 14 and a spreading membrane 18 configured to be positioned between the microneedle assembly 200 and the reservoir 14.

In general, it should be appreciated that any suitable drug formulation(s) may be retained within and delivered via the disclosed device 10. As used herein, the term "drug formulation" is used in its broadest sense and may include, but is not limited to, any drug (e.g., a drug in neat form) and/or any solution, emulsion, suspension and/or the like containing a drug(s). Similarly, the term "drug" is used in its broadest sense and includes any compound having or perceived to have a medicinal benefit, which may include both regulated and unregulated compounds. For example, suitable types of drugs may include, but are not limited to, biologics, small molecule agents, vaccines, proteinaceous compounds, anti-infection agents, hormones, compounds regulating cardiac action or blood flow, pain control agents and so forth. One of ordinary skill in the art should readily appreciate that various ingredients may be combined together in any suitable manner so as to produce a compound having or perceived to have a medicinal benefit.

The drug delivery device 10 is configured to contain a liquid drug formulation. The drug formulation may include one or more drugs and, as desired, one or more additional compounds to assist with the delivery, stability, maintenance and/or function of the drug. The drug formulation suitable for use with the present invention comprises a liquid. In several embodiments, the drug formulation is a liquid at 37° C. (body temperature) or, in another embodiment, liquid at 20° C. (room temperature). Additionally, the liquid drug formulation, in certain embodiments, has a dynamic viscosity at body temperature that is less than 20 Pascal-seconds (Pa·S), or in other embodiments less than 10 Pa·S or still further in other embodiments less than 1 Pa·S; and in other embodiments the drug formulation may have a viscosity between about $1\times10^2$ Pa·S and $1\times10^{-4}$ Pa·S or still further a viscosity between about $1\times10^1$ Pa·S and $1\times10^{-3}$ Pa·S. The particular drug dosage utilized will vary accordingly with known factors such as the particular drug, the age and/or weight of the patient, the disease and/or condition being treated, and so forth.

In several embodiments, the drug formulation may also include one or more pharmaceutically acceptable carriers. The term "carriers' as used herein includes, but is not limited to, acceptable solvents, diluents, excipients, adjuvants, vehicles, solubilization aids, viscosity modifiers, preservatives and other agents known to a person skilled in the art for the formation of pharmaceutically formulations. Various non-limiting examples of commonly used carriers are described herein below.

In certain embodiments, the drug formulation may include one or more solvents. Suitable solvents may, for example, include, but are not limited to, acetone, alcohol, amylene hydrate, butyl alcohol, corn oil, cottonseed oil, ethyl acetate, glycerin, hexylene glycol, isopropyl alcohol, isostearyl alcohol, methyl alcohol, methylene chloride, mineral oil, peanut oil, phosphoric acid, polyethylene glycol, polyoxypropylene 15 stearyl ether, propylene glycol, propylene glycol diacetate, sesame oil, purified water and/or any other acceptable solvents.

The drug formulation may also include one or more surface-active agents, such as one or more surfactants and/or emulsifiers. The surface-active agents may be used to provide stability for the drug formulation, to enhance or modify the existing properties of the drug formulation (e.g., to modify the surface energy of the drug formulation) and/or for any other suitable purpose. Suitable surface-active agents may, for instance, include, but are not limited to, glyceryl trioleate, acetylated sucrose distearate, sorbitan trioleate, polyoxyethylene (1) monostearate, glycerol monooleate, sucrose distearate, polyethylene glycol (50) monostearate, octylphenoxypoly (ethyleneoxy) ethanol, diglycerin penta-isostearate, sorbitan sesquioleate, hydroxylated lanolin, lanolin, triglyceryl diisostearate, polyoxyethylene (2) oleyl ether, calcium stearoyl-2-lactylate, methyl glucoside sesquistearate, sorbitan monopalmitate, methoxy polyethylene glycol-22/dodecyl glycol copolymer (Elfacos E200), polyethylene glycol-45/dodecyl glycol copolymer (Elfacos ST99), polyethylene glycol 400 distearate and glyceryl stearate; alcohols, such as cetyl alcohol and lanolin alcohol; myristates, such as isopropyl myristate; cetyl palmitate; cholesterol; stearic acid; propylene glycol; glycerine, sorbitol, cetyl hydroxyethylcellulose, ceteth-20 (a polyethylene glycol derivative of cetyl alcohol), cetearyl olivate and/or any other suitable surface-active agents.

Addition, the drug formulation may also include one or more viscosity modifying agents, such as one or more stiffening or thickening agents. For instance, suitable viscosity modifying agents may include, but are not limited to, suitable waxes, such as cetyl esters wax, emulsifying wax, microcrystalline wax, white wax and yellow wax, myristyl alcohol, parafin, synthetic parafin, suitable natural gums, such as xanthan gum, talha gum, tragacanth gum, locust bean gum, guar gum, Irish moss gum, ghatti gum, furcelleran gum, carrageenan gum, arabic gum, alginic acid gum, agar gum, alginate gum, synthetic polymers and/or any other suitable viscosity modifying agents.

Moreover, the drug formulation may also include one or more pH control or buffering agents to maintain or provide a desired pH of the drug formulation. Suitable pH control or buffering agents may, for example, include, but are not limited to calcium, acetate, potassium metaphosphate, potassium phosphate monobasic, and tartaric acid and/or any other suitable pH control or buffering agents (e.g., various suitable weak acids and/or bases).

The drug formulation may also include one or more chelating agents to help maintain the ionic strength of the drug formulation and bind to and effectively remove any destructive compounds and metals. For instance, suitable chelating agents may include, but are not limited to, edetate dipotassium, edetate disodium edetic acid and/or any other suitable chelating agents.

In addition, the drug formulation may include one or more antimicrobial additives, such as one or more antimicrobial agents and/or one or more antimicrobial preservatives. For instance, suitable antimicrobial agents may include, but are not limited to, benzyl alcohol, chlorobutanol, phenylethyl alcohol, phenylmercuric acetate, potassium sorbate, and sorbic acid and/or any other suitable antimicrobial agents. Similarly, suitable antimicrobial preservatives may include, but are not limited to alkyl esters of p-hydroxybenzoic acid, propionate salts, phenoxyethanol, methylparaben sodium, propylparaben sodium, sodium dehydroacetate, benzalkonium chloride, benzethonium chloride, benzyl alcohol, hydantoin derivatives, quaternary ammonium compounds and cationic polymers, imidazolidinyl urea, diazolidinyl urea, trisodium ethylenediamine tetracetate (EDTA) and/or any other suitable antimicrobial preservatives.

It should be appreciated that the drug formulation may be modified by the selection of various ingredients, most notably the solvent and surface-active agents, to achieve the desired surface energy characteristics described herein in order to achieve a passive flow drug delivery device wherein the drug formulation will spontaneously flow along the microneedle channels the majority of and/or substantially the entire length of the channels.

Figure 9:
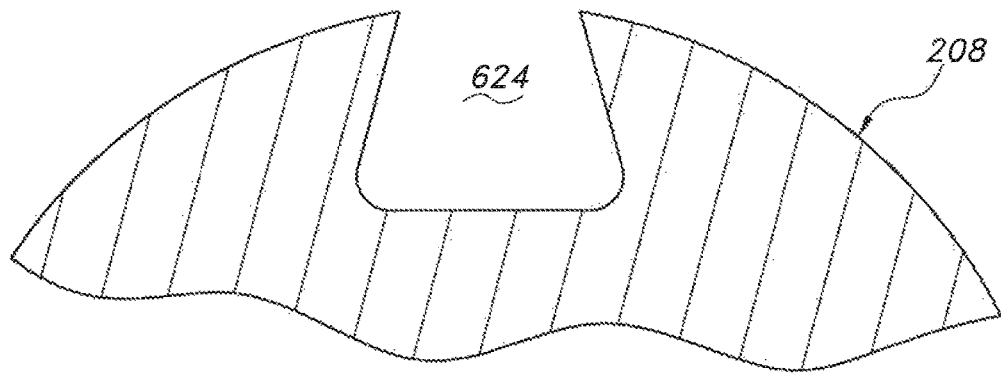
FIG. 9 illustrates a partial, cross-sectional view of a microneedle having a channel defining a rounded trapezoidal shaped cross-section in accordance with aspects of the present subject matter, particularly illustrating the trapezoidal shape being inverted as compared to the trapezoidal shape channel shown in FIG. 6.

Referring still to FIGS. 10-12, the microneedle assembly 200 may generally be configured the same as or similar to that described above with references to FIGS. 1-9. For example, the assembly 200 may include a plurality of microneedles 208 (FIG. 1) extending from a support 202 (FIG. 1), with each microneedle 208 defining one or more open channels 224, 324, 424, 524, 624 (FIGS. 1 and 61-9). As indicated above, the overall device composition and structure, including the cross-sectional geometry of each channel, may be configured to provide a passive flow device in which the drug formulation will spontaneously flow from the reservoir 14 down and into the length of the channels in the microneedles 208 and, from the channel openings into the body of the patient.

As indicated above, it should be appreciated that the disclosed device 10 may generally have any suitable configuration that allows for a passive fluid flow of the drug formulation through the microneedles 208. As used herein, the term "passive fluid flow" refers to an innate fluid flow through the microneedles 208 that is driven primarily and/or predominantly by forces associated with the relative surface tension of the drug formulation, the surface energy of the microneedle material and bodily absorption. In several embodiments, the device 10 may be configured such that the flow of the drug formulation is passively driven from the reservoir 14 to the microneedle assembly 200 and then through the microneedles 208. In such embodiments, the passively driven flow would not include fluid flows resulting substantially from the pressurization and/or the application of an external force against the drug formulation and/or the reservoir 14 to push or otherwise force the drug formulation out of the reservoir 14 and into the microneedles 208, such as fluid flows resulting from the use of a pump or any other suitable active device that directly or indirectly applies a force against the drug formulation. Alternatively, the device 10 may be configured such that drug formulation is only passively driven through the microneedles 208, with the fluid flow of the drug formulation from the reservoir 14 to the microneedle assembly 200 resulting substantially from the pressurization and/or the application of an external force against the drug formulation and/or the reservoir 14.

In several embodiments, the reservoir 14 of the disclosed device 10 may generally be configured as a solid block or body defining a plurality of capillaries or passages for initially retaining the drug formulation prior to the subsequent delivery of the formulation into the microneedle assembly 200. Specifically, as shown in FIGS. 10 and 11, the reservoir 14 may include a top surface 36 and a bottom surface 38 and may define a plurality of passages 40 extending between the top and bottom surfaces 36, 38. The body of the reservoir 14, itself, may generally define any suitable shape and/or may have any suitable configuration that the permits the reservoir 14 to function as described herein. For example, as shown in FIG. 10, in one embodiment, the reservoir body may include an upper portion 42 defining a generally rectangular shape that extends from the top surface 36 to a central peripheral edge 44 of the reservoir 14 and a lower portion 46 defining a generally rectangular shape that extends from the peripheral edge 44 to the bottom surface 38, with the lower portion 46 being recessed relative to upper portion 42. However, in other embodiments, the body of the reservoir 14 may have any other suitable configuration and/or define any other suitable shape.

The passages 40 defined through the reservoir 14 may generally be configured such that the drug formulation is retained within the reservoir 14 against gravity until it is drawn out passively due to skin absorption and/or a capillary-driven flow through the microneedles 208. Specifically, in several embodiments, the dimensions of each passage 40, along with the drug formulation, itself, may be selected to permit the drug formulation to be retained within the passages 40 due to capillary action until a negative pressure is generated within the microneedle assembly 200 that is sufficient to draw the drug formulation out of the passages 40 and into the microneedles 208. Smaller capillaries produce greater capillary forces and, thus, the cross-sectional dimension 41 (FIG. 11) of each passage 40 (e.g., diameter, width, etc.) may be carefully selected such that a capillary pressure is generated within each passage 40 that is sufficient to initially retain the drug formulation within the passages 40. For example, in several embodiments, the cross-sectional area of each passage 40 may range from about 1,000 square microns ($um^2$) to about 125,000 $um^2$, such as from about 1,250 $um^2$ to about 60,000 $um^2$ or from about 6,000 $um^2$ to about 20,000 $um^2$ and any other subranges therebetween.

Moreover, the capillary pressure required to hold the drug formulation against gravity may also vary as a function of the height 43 (FIG. 12) of the passages 40. Thus, in several embodiments, the height 43 of each passage 40 may also be carefully selected to ensure that the drug formulation is initially retained within the passages 40. For example, in a particular embodiment, the height 43 of each passage 40 may be less than about 3 centimeters (cm), such as a height ranging from about 1.5 cm to about 0.5 cm or from about 1 cm to about 0.5 cm and any other subranges therebetween.

It should be appreciated that the particular number of passages 40 formed in the reservoir 14 may generally vary depending on numerous factors, including, but not limited to, the cross-sectional dimension 41 of each of the passages 40 and the total volume of the drug formulation desired to be retained within the reservoir 14. However, in a particular embodiment of the present subject matter, the number of passages 40 formed in the reservoir 14 may range from about 10 passages per square centimeter ($cm^2$) to about 1,500 passages per $cm^2$, such as from about 50 passages per $cm^2$, to about 1250 passages per $cm^2$ or from about 100 passages per $cm^2$ to about 500 passages per $cm^2$ and any other subranges therebetween. It should also be appreciated that the passages 40 may be configured to define any suitable cross-sectional shape. For example, in one embodiment, each passage 40 may define a semi-circular or circular shape. In another embodiment, each passage 40 may define a non-circular shape, such as a "v" shape or any other suitable cross-sectional shape.

Additionally, the capillary pressure within the passages 40 may also be affected by the contact angle defined between the drug formulation and the passages 40, which, as indicated above, is generally determined by the surface energy of the passage material and the surface tension of the drug formulation. As such, the material used to form the reservoir body itself may be carefully selected to further enhance the drug delivering capabilities of the disclosed device 10. Specifically, it may be desirable for the selected material to have a sufficient affinity for the drug formulation to allow it to be initially retained within the passages 40 while still allowing the drug formulation to be passively drawn out of the passages 40 by the negative pressure generated within the microneedle assembly 12. In several embodiments, the material used to form the reservoir 14 may be selected such that a contact angle is defined between the drug formulation and the passages 40 that is less than about 90 degrees, such as less than about 60 degrees or less than about 30 degrees and any other subranges therebetween. In considering these ranges, it has been found that certain nylon materials (e.g., nylon 6), poly-acrylic materials, silicon materials, glass materials and thermoplastic materials may provide such desired characteristics. However, it should be appreciated that the reservoir 14 may generally be formed from any suitable material that permits it to function as described herein.

It should be appreciated that the capillary pressure within the passages 40 may generally be smaller (i.e., less negative or closer to a zero pressure) than the capillary pressure within the channels of the microneedles 208. However, as indicated above, it is desirable for the capillary forces within the passages 40 to be sufficient to initially retain the drug formulation within the passages 40 against gravity. Thus, in several embodiments, the capillary pressure within each passage 40 may generally be large enough to generate a capillary force that is greater than the gravitational force acting on the drug formulation (preferably greater than two times the gravitational force).

It should also be appreciated that the drug formulation may be supplied to the reservoir 14 in a variety of different ways. For example, in several embodiments, the drug formulation may be supplied to reservoir 14 via an inlet channel 48 defined through a portion of the reservoir body. For example, as shown in FIGS. 10 and 12, in one embodiment, an inlet channel 48 may formed within the reservoir 14 that extends between an inlet 50 defined through a projection 52 extending outwardly from the upper portion 42 of the reservoir 14 and an outlet 54 defined through the bottom surface 38 of the reservoir 14. In such an embodiment, a suitable conduit or tube 56 (FIG. 16) may be configured to be received within the inlet 50 and may be in fluid communication with a suitable drug source (e.g., a syringe containing the drug formulation) such that the drug formulation may be directed into the inlet channel 48 and expelled from the outlet 54 along the bottom surface 38 of the reservoir 14. The drug formulation may then be drawn upwards into the passages 40 via capillary action.

However, in others embodiments, the drug formulation may be supplied to the reservoir 14 using any other suitable method. For example, in another embodiment, the lower portion 46 of the reservoir 14 may simply be placed in fluid communication with the drug formulation (e.g., by dipping the reservoir 14 into a container holding the drug formulation) to allow the formulation to flow upward into the passages 40 via capillary action.

Referring still to FIGS. 10-12, the reservoir frame 16 may generally be configured as a rigid or semi-rigid body defining a frame opening 58 configured to receive at least a portion of the reservoir 14, thereby allowing the reservoir 14 to be supported within the frame 16. Thus, it should be appreciated that, in several embodiments, the frame opening 58 may generally be formed in the frame 16 so as to define a shape corresponding to the overall shape of the body of the reservoir 14. For example, as shown in FIG. 10, an upper portion 60 of the frame opening 58 may be configured to define a generally rectangular-shaped opening corresponding to the rectangular shape of the upper portion 42 of the reservoir 14. Similarly, a lower portion 62 of the frame opening 58 may be reduced in size so as to define an opening generally corresponding to shape of the recessed, lower portion 46 of the reservoir 14. Additionally, as shown in FIG. 10, the frame 16 may also define an inlet recess 64 configured receive the outwardly extending projection 52 of the reservoir 14. As such, when the reservoir 14 is received within the frame opening 58, the reservoir 14 may be vertically supported within the frame 16.

Additionally, in several embodiments, the reservoir frame 16 may be configured to be coupled to the microneedle assembly 200. For example, as shown in FIG. 12, a suitable adhesive 66 (e.g., a pressure sensitive adhesive) may be applied between a bottom surface 68 of the reservoir frame 16 and the periphery of the top surface of the microneedle assembly 200 (i.e., the top surface 204 (FIG. 1) of the support 202) to secure the microneedle assembly 200 to the reservoir frame 16. However, in other embodiments, the microneedle assembly 200 may be configured to be coupled to a portion of the reservoir 14 (e.g., along the outer periphery of the bottom surface 38 of the reservoir 14).

As indicated above, the device 10 may also include a spreading membrane 18 disposed between the microneedle assembly 200 and the reservoir 14. Specifically, as shown in FIG. 12, the spreading membrane 18 may be disposed at the interface defined between the top surface of the microneedle assembly 200 and the bottom surface 38 of the reservoir 14. In general, the spreading membrane 18 may be fabricated from any suitable permeable, semi-permeable or microporous material(s) (e.g., a nylon filter mesh) that allows for the flow and/or distribution of the drug formulation therethrough. For example, in one embodiment, the material used to form the spreading membrane 18 may have an average pore size of from about 0.01 micron to about 1000 microns, such as from about 1 micron to about 500 microns or from about 20 microns to about 200 microns and any other subranges therebetween. Regardless, the spreading membrane 18 may be configured to distribute the drug formulation evenly along the bottom surface 38 of the reservoir 14. For example, as shown in the illustrated embodiment, the drug formulation flowing through the inlet channel 48 may be expelled via the outlet 54 into the spreading membrane 18, which may then distribute the formulation along the bottom surface 38 of reservoir 38 so that it may be drawn upwards into the passages 40 via capillary action.

Referring now to FIGS. 13-16, several views of additional components that may also form all or part of the disclosed drug delivery device 10 are illustrated in accordance with aspects of the present subject matter. As shown, in addition to the microneedle assembly 200, reservoir 14, reservoir frame 16 and spreading membrane 18, the device 10 may also include an outer housing 112 configured to at least partially surround and/or encase the various components of the device 10. For example, as particularly shown in FIGS. 13 and 16 the housing 112 may include an upper housing portion 114 defining an open volume for housing the various device components. The upper housing portion 112 may generally be configured to define any suitable shape. For instance, as shown in the illustrated embodiment, the upper housing portion 114 may define a semi-circular or dome shape. However, in other embodiments, the upper housing portion 114 may have any other suitable shape that defines an open volume for housing the various components of the device 10.

In addition, the housing 112 may include a lower housing portion 116 configured to be positioned adjacent to the user's skin when the device 10 is in use. As shown, the lower housing portion 116 may generally be configured as a flange or projection extending outwardly from the bottom periphery of the upper portion 114 of the housing 112. In several embodiments, the lower housing portion 116 may be configured to be attached to the user's skin using a skin attachment means. For example, in one embodiment, a suitable adhesive 118 may be applied to a bottom surface 120 of the lower housing portion 116. As such, when the lower housing portion 116 is placed onto the user's skin, the adhesive may secure the housing 112 to the skin.

Figure 14:
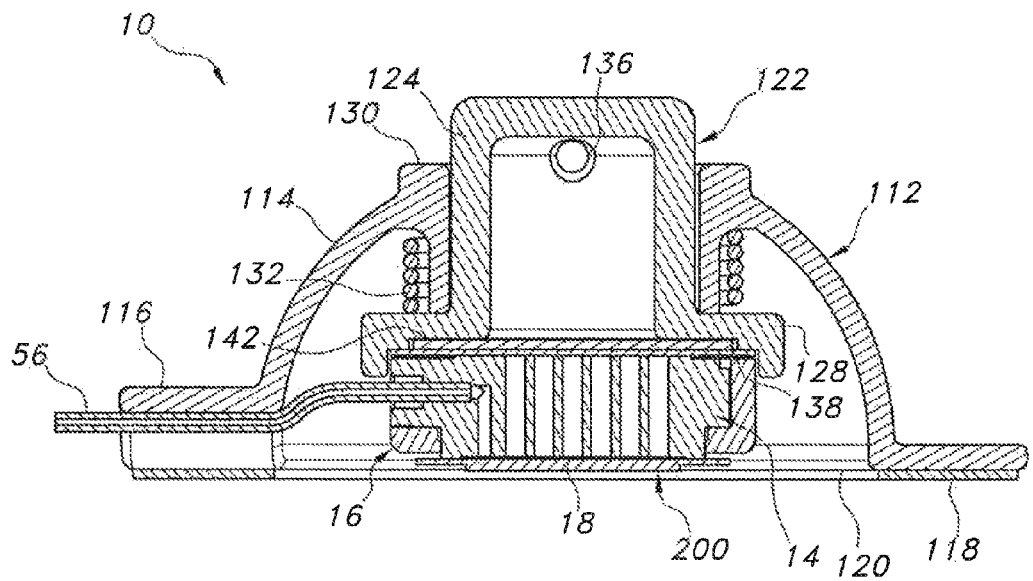
FIG. 14 illustrates a cross-sectional view of the device components shown in FIG. 13 taken about line 14-14, particularly illustrating a plunger of the device in an un-actuated position.
Figure 15:
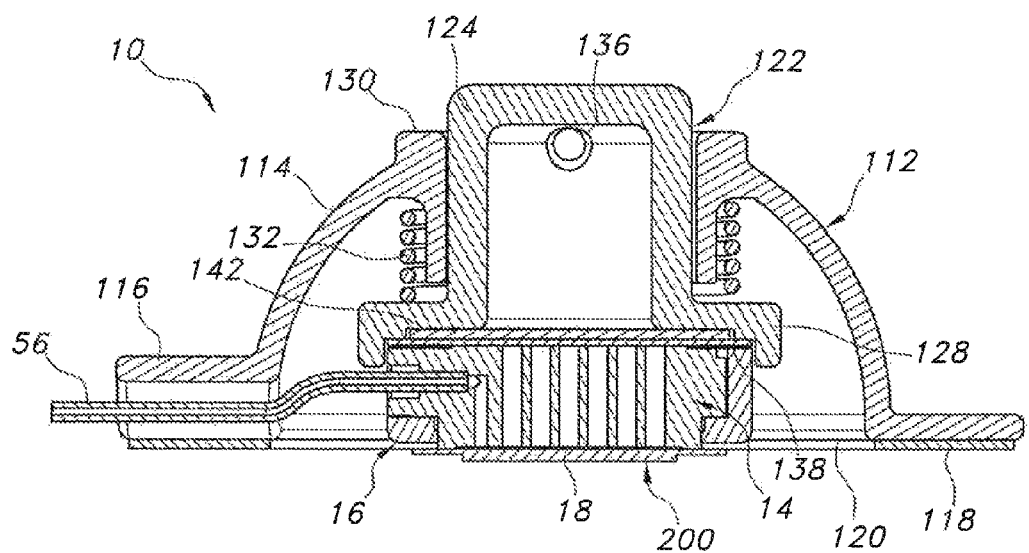
FIG. 15 illustrates another cross-sectional view of the device components shown in FIG. 13, particularly illustrating the plunger in an actuated position.
Figure 16:
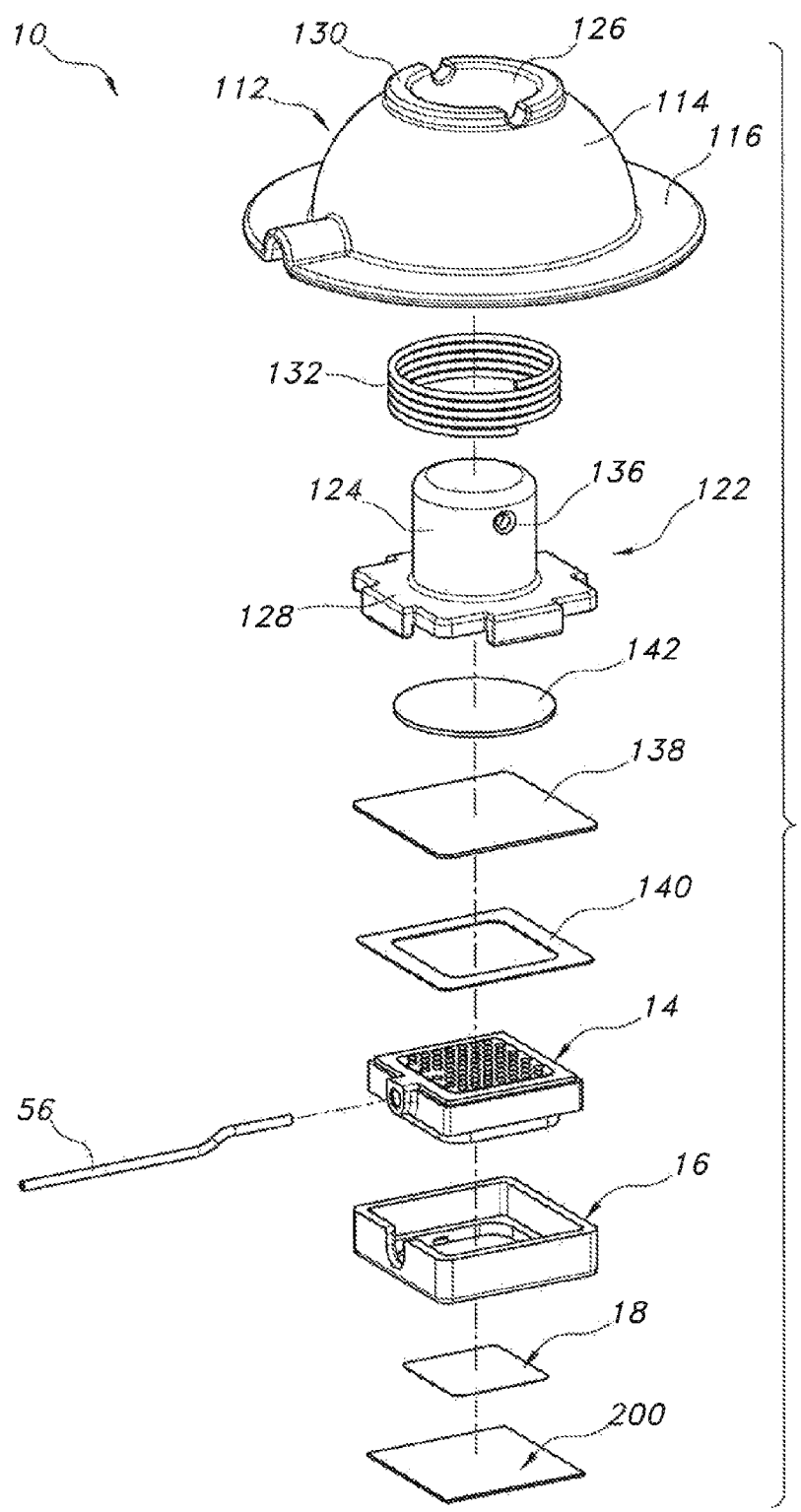
FIG. 16 illustrates an exploded perspective view of the device components shown in FIGS. 13-15.

Moreover, the device 10 may also include a plunger 122 configured to be moved relative to the housing 112 between un-actuated position (FIG. 14), wherein the bottom of the microneedle assembly 200 is generally aligned with or recessed relative to the bottom surface 120 of the lower housing portion 116 and an actuated position (FIG. 15), wherein the microneedle assembly 200 extends outward beyond the bottom surface 120 of the lower housing portion 116, thereby allowing the microneedles 208 of the microneedle assembly 200 to penetrate the user's skin. As shown in FIGS. 14-16, in one embodiment, the plunger 122 may generally include a cylindrical top portion 124 configured to be slidably received within a corresponding opening 126 defined in the housing 112 and a flattened bottom portion 126 configured to engage or otherwise apply a force against the reservoir 14 and/or reservoir frame 16. In such an embodiment, when the top portion 124 of the plunger 122 is moved downward within the opening 126 relative to a top surface 130 of the housing 112, the bottom portion 128 of the plunger 122 may apply a force against the reservoir 14 and/or reservoir frame 16 that pushes the microneedle assembly 200 downward into the user's skin.

Figure 13:
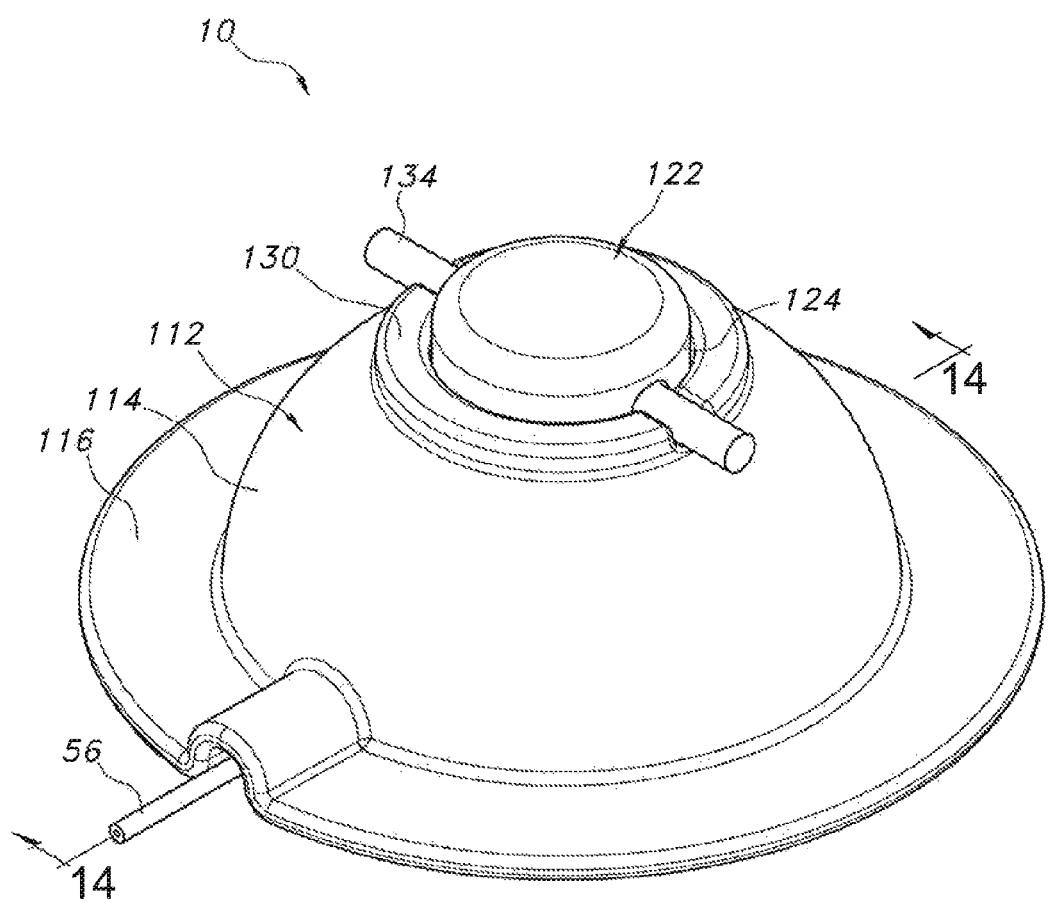
FIG. 13 illustrates a perspective, assembled view of various components that may be included within another embodiment of a drug delivery device in accordance with aspects of the present subject matter.

It should be appreciated that the plunger 122 may be configured to be pushed downward against the reservoir 14 and/or reservoir frame 16 using any suitable means known in the art. For example, as shown in the illustrated embodiment, a spring 132 may be positioned between the bottom portion 128 of the plunger 122 and the upper housing portion 114 of the housing 112 so as apply a downward force against the plunger 122. In such an embodiment, a lock pin and/or other locking mechanism may be configured to maintain the plunger 122 in the un-actuated position when the device 10 is not use. For example, as shown in FIG. 13, a lock pin 134 may be configured to extend through an opening 136 defined in the plunger 122 so as to engage opposing sides of the upper housing portion 114, thereby preventing the plunger 122 from moving relative to the housing 112. However, when the lock pin 134 is removed, the force applied by the spring 132 may push the plunger 122 downward into the actuated position, thereby causing the microneedle assembly 12 to be moved in the direction of the user's skin.

In one embodiment, the configuration of the spring 132 (including its length and spring constant) may be selected such that the downward force transmitted to the microneedle assembly 200 is sufficient to cause the microneedles 208 to penetrate the user's skin and remain therein during delivery of the drug formulation without any additional force applied to the plunger 122. Alternatively, the configuration of the spring 132 may be selected so that an additional downward force is required to cause the microneedles 208 to penetrate the user's skin and/or remain therein during delivery of the drug formulation. In such an embodiment, the additional downward force may be applied, for example, by the user pressing down against the top of the plunger 122.

It should be appreciated that, in addition to the downward force applied by the spring 132, a reactive, upward force may also be applied by the spring 132 against the housing 112. Due to the configuration of the disclosed device 10, such upward force may generally be transmitted through the housing 112 to the user's skin via the adhesive 118 used to secure the housing 112 to the user. As such, the user's skin may be tightened as it is pulled upward around the periphery of the housing 112, thereby enhancing the ease in which the microneedles 208 may be inserted into the skin.

It should also be appreciated that, in alternative embodiments, the plunger 122 may be moved relative to the housing 112 using any other suitable means known in the art. For example, in one embodiment, the user simply may apply finger pressure to the top of the plunger 122 to push it downward. Moreover, in other embodiments, the disclosed device 10 may include any other suitable means known in the art for generating and/or applying pressure to the microneedle assembly 12 and/or the reservoir 14. For instance, fluid pressure (e.g., pressurized air derived from reactions and/or pumped into the device 10) may be used to apply pressure to the microneedle assembly 200 and/or the reservoir 14. In another embodiment, any other suitable device and/or actuator (e.g., a turn/crank mechanism, a displacement cylinder and/or the like) may be used to apply a mechanical force against the microneedle assembly 200 and/or the reservoir 14.

Additionally, it should be noted that, since the reservoir 14 is designed such that the drug formulation is retained within the passages 40, the disclosed plunger 122 does not apply a significant force against the drug formulation itself. Rather, when a downward force is applied by the plunger 122, the force is transmitted through the body of the reservoir 14 and/or the reservoir frame 16. Accordingly, the microneedles 208 may be pressed into the user's skin without increasing the pressure of the drug formulation or otherwise pushing downward onto the drug formulation, thereby preventing the drug formulation from being forced through the microneedles 26 at an undesirable flow rate.

Referring still to FIGS. 13-16, the device 10 may also include a filter 138 configured to allow air (including any air rising upward from the microneedle assembly 200) to be vented from the reservoir 14. As shown FIGS. 14 and 15, the filter 138 may be configured to be positioned directly adjacent to the top surface 36 of the reservoir 14 so as to cover the top end of each passage 40. In such an embodiment, the filter 138 may be attached to the reservoir 14 around the periphery of its top surface 36. For example, as shown in FIGS. 14-16, a suitable adhesive 140 (e.g., a pressure sensitive adhesive) may be disposed between the filter 138 and the top surface 36 in order to secure the filter 138 to the reservoir 16.

In general, it should be appreciated that the filter 138 may be formed from any suitable air permeable material that at least partially resists and/or repels the passage of the drug formulation therethrough. In certain embodiments, it may be desirable for the filter 138 to readily allow the passage of air and to completely or substantially prevent the passage of fluids including any carriers or diluents such as alcohol or water. For example, in several embodiments, the filter 138 may be formed from a highly hydrophobic and oleophobic material(s), such as certain acrylic copolymer membranes, other hydrophobic polymer(s) and/or any other suitable material(s).

Additionally, as shown in FIG. 16, in several embodiments, a rigid or semi-rigid screen 142 (e.g., a metal wire mesh) may be positioned between the filter 138 and the plunger 122. Thus, as the plunger 122 is pushed downward against the screen 142 (e.g., via the force applied by the spring 132), the screen 142 may maintain the filter 138 flat against the top surface 36 of the reservoir 14 while permitting air to pass therethrough. As such, the filter 138 may completely cover/seal the top of each passage 40, thereby allowing the filter 138 to serve as a means for resisting or repelling the flow of the drug formulation along the top surface 36 of the reservoir 14.

It should be appreciated that, in various embodiments of the present subject matter, the disclosed device 10 may include all or any combination of the components shown in FIGS. 10-16. For instance, in one embodiment, the device 10 may simply comprise the microneedle assembly 200, the reservoir 14 and the spreading membrane 18 or any other suitable combination of the disclosed components.

It should also be appreciated that, although the reservoir 14 described above is configured as a solid block or body defining a plurality of passages 40 for retaining the drug formulation, the reservoir may generally have any suitable configuration that allows it to retain the drug formulation prior to its subsequent delivery to the microneedle assembly 200. For example, in alternative embodiments, the reservoir 14 may simply be configured as a container defining an open volume or cavity for retaining the drug formulation. In such embodiments, the reservoir 14 may be a rigid or a semi-rigid member (e.g., by being configured as a rigid, hollow container) or the reservoir 14 may be a flexible bladder. In a further embodiment, the reservoir 14 may be configured as a solid container or matrix through which the drug formulation is capable of being directed, such as a permeable, semi-permeable or microporous solid matrix. In still a further embodiment, the reservoir 14 may comprise a flexible bladder contained within or shielded by a rigid member.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they include structural elements that do not differ from the literal language of the claims, or if they include equivalent structural elements with insubstantial differences from the literal languages of the claims.

What is claimed is:

1. A drug delivery device, comprising:
a reservoir containing a liquid drug formulation; and
a microneedle assembly in fluid communication with the reservoir, the microneedle assembly including a support defining an upper surface and a lower surface, the microneedle assembly further including a plurality of microneedles extending from the lower surface, each microneedle defining an open channel for receiving the drug formulation, the open channel having a normalized hydraulic radius ranging from 0.1 to 0.8, the open channel further having a liquid-to-solid interfacial energy and a liquid-to-vapor interfacial energy when a fixed volume of the drug formulation is received therein,
wherein the drug formulation and a cross-sectional geometry of the open channel is selected and configured based on an interaction between the drug formulation and the open channel such that the liquid-to-solid interfacial energy exceeds the liquid-to-vapor interfacial energy as a fluid length of the fixed volume of drug formulation is increased within the open channel.

2. The drug delivery device as in claim 1, wherein the liquid-to-solid interfacial energy is determined according to the following equation:

$$E_{LS} = -L * L_g * \gamma * \cos(\theta)$$

wherein, $E_{LS}$ corresponds to the liquid-to-solid interfacial energy, L corresponds to the fluid length, $L_g$ corresponds to a liquid/solid interface length of the drug formulation within the open channel, γ corresponds to a liquid surface tension of the drug formulation within the open channel and θ corresponds to a contact angle defined between the drug formulation and the open channel.

3. The drug delivery device as in claim 1, wherein the liquid-to-vapor interfacial energy is determined according to the following equation:

$$E_{LV} = L*L_S*\gamma$$

wherein, $E_{LV}$ corresponds to the liquid-to-vapor interfacial energy, L corresponds to the fluid length, $L_S$ corresponds to a liquid/vapor interface length of the drug formulation within the open channel and γ corresponds to a liquid surface tension of the drug formulation within the open channel.

4. The drug delivery device as in claim 1, wherein the drug formulation and the cross-sectional geometry of the open channel is selected and configured such that the following constraint is satisfied:

$$\frac{d}{dL}[E_{LV} + E_{LS}]_V < 0$$

wherein, $E_{LV}$ corresponds to the liquid-to-vapor interfacial energy, $E_{LS}$ corresponds to the liquid-to-solid interfacial energy, L corresponds to the fluid length of the drug formulation and V corresponds to the fixed volume of the fluid.

5. The drug delivery device as in claim 4, wherein the open channel defines a substantially parabolic shaped cross-section.

6. The drug delivery device as in claim 5, wherein the drug formulation and the cross-sectional geometry of the open channel is selected and configured such that at least one of the following constraints is satisfied:

$$\frac{\pi}{4} - \frac{\varphi}{2} \leq \theta \leq \frac{\pi}{2} - \varphi$$

$$\theta < \frac{\pi}{4} - \frac{\varphi}{2}$$

wherein, θ corresponds to a contact angle defined between the drug formulation and the open channel and 2*φ corresponds to a groove angle of the open channel.

7. The drug delivery device as in claim 4, wherein the open channel defines a substantially trapezoidal shaped cross-section.

8. The drug delivery device as in claim 7, wherein the drug formulation and the cross-sectional geometry of the open channel is selected and configured such that at least one of the following constraints is satisfied:

$$\frac{\pi}{2} - 2.3*\theta \leq \varphi \leq \frac{\pi}{2} - \theta$$

$$\varphi < \frac{\pi}{2} - 2.3*\theta$$

wherein, θ corresponds to a contact angle defined between the drug formulation and the open channel and 2*φ corresponds to a groove angle of the open channel.

9. The drug delivery device as in claim 1, wherein the open channel defines a substantially parabolic shaped cross-section, wherein a distance from a vertex of the cross-sectional shape to a focal point of the cross-sectional shape is equal to or less than 50% of a depth of the open channel.

10. The drug delivery device as in claim 1, wherein each microneedle has a skin contact area ranging from about 1,500 um$^2$ to about 262,500 um$^2$.

11. A drug delivery device, comprising:
a reservoir configured to initially retain a drug formulation; and
a microneedle assembly in fluid communication with the reservoir, the microneedle assembly being configured such that a passive fluid flow of the drug formulation is directed through the microneedle assembly, the microneedle assembly including a support defining an upper surface and a lower surface, the microneedle assembly further including a plurality of microneedles extending from the lower surface, each microneedle defining an open channel for receiving the drug formulation, the open channel having a normalized hydraulic radius ranging from 0.1 to 0.8, the open channel further having a liquid-to-solid interfacial energy and a liquid-to-vapor interfacial energy when a fixed volume of the drug formulation is received therein,
wherein the drug formulation and a cross-sectional geometry of the open channel is selected and configured based on an interaction between the drug formulation and the open channel such that the liquid-to-solid interfacial energy exceeds the liquid-to-vapor interfacial energy as a fluid length of the fixed volume of drug formulation is increased within the open channel.

12. The drug delivery device as in claim 11, wherein the passive fluid flow of the drug formulation through the microneedle assembly derives from the forces associated with at least one of a relative surface tension of the drug formulation, a surface energy of a material forming each microneedle or bodily absorption.

13. The drug delivery device as in claim 11, wherein the reservoir includes a top surface and a bottom surface, the reservoir defining a plurality of passages extending between the top and bottom surfaces, the passages being configured such that the drug formulation is retained within the passages against gravity until a negative pressure is generated within the microneedle assembly that draws the drug formulations out of the reservoir and into the open channel of each microneedle.

14. The drug delivery device as in claim 11, further comprising a spreading membrane disposed between the microneedle assembly and the reservoir, the spreading membrane being configured to distribute the drug formulation along a bottom surface of the reservoir.

15. The drug delivery device as in claim 11, wherein the liquid-to-solid interfacial energy is determined according to the following equation:

$$E_{LS} = -L*L_g*\gamma*\cos(\theta)$$

wherein, $E_{LS}$ corresponds to the liquid-to-solid interfacial energy, L corresponds to the fluid length, $L_g$ corresponds to a liquid/solid interface length of the drug formulation within the open channel, γ corresponds to a liquid surface tension of the drug formulation within the open channel and θ corresponds to a contact angle defined between the drug formulation and the open channel.

16. The drug delivery device as in claim 11, wherein the liquid-to-vapor interfacial energy is determined according to the following equation:

$$E_{LV} = L * L_S * \gamma$$

wherein, $E_{LV}$ corresponds to the liquid-to-vapor interfacial energy, L corresponds to the fluid length, $L_S$ corresponds to a liquid/vapor interface length of the drug formulation within the open channel and γ corresponds to a liquid surface tension of the drug formulation within the open channel.

17. The drug delivery device as in claim 11, wherein the drug formulation and the cross-sectional geometry of the open channel is selected and configured such that the following constraint is satisfied:

$$\frac{d}{dL}[E_{LV} + E_{LS}]_V < 0$$

wherein, $E_{LV}$ corresponds to the liquid-to-vapor interfacial energy, $E_{LS}$ corresponds to the liquid-to-solid interfacial energy, L corresponds to the fluid length of the drug formulation and V corresponds to the fixed volume of the fluid.

18. The drug delivery device as in claim 17, wherein the open channel defines a substantially parabolic shaped cross-section.

19. The drug delivery device as in claim 18, wherein the drug formulation and the cross-sectional geometry of the open channel is selected and configured such that at least one the following constraints is satisfied:

$$\frac{\pi}{4} - \frac{\varphi}{2} \leq \theta \leq \frac{\pi}{2} - \varphi$$

$$\theta < \frac{\pi}{4} - \frac{\varphi}{2}$$

wherein, θ corresponds to a contact angle defined between the drug formulation and the open channel and 2*φ corresponds to a groove angle of the open channel.

20. The drug delivery device as in claim 17, wherein the open channel defines a substantially trapezoidal shaped cross-section.

21. The drug delivery device as in claim 20, wherein the drug formulation and the cross-sectional geometry of the open channel is selected and configured such that at least one of the following constraints is satisfied:

$$\frac{\pi}{2} - 2.3 * \theta \leq \varphi \leq \frac{\pi}{2} - \theta$$

$$\varphi < \frac{\pi}{2} - 2.3 * \theta$$

wherein, θ corresponds to a contact angle defined between the drug formulation and the open channel and 2*φ corresponds to a groove angle of the open channel.

22. The drug delivery device as in claim 11, wherein the open channel defines a substantially parabolic shaped cross-section, wherein a distance from a vertex of the cross-sectional shape to a focal point of the cross-sectional shape is equal to or less than 50% of a depth of the open channel.

23. The drug delivery device as in claim 11, wherein each microneedle has a skin contact area ranging from about 1,500 um$^2$ to about 262,500 um$^2$.

24. A drug delivery device, comprising:
a reservoir containing a liquid drug formulation; and
a microneedle assembly in fluid communication with the reservoir, the microneedle assembly including a support defining an upper surface and a lower surface, the microneedle assembly further including a plurality of microneedles extending from the lower surface, each microneedle defining an open channel for receiving the drug formulation and having a skin contact area ranging from about 1,500 um$^2$ to about 262,500 um$^2$, the open channel having a liquid-to-solid interfacial energy and a liquid-to-vapor interfacial energy when a fixed volume of the drug formulation is received therein,
wherein a relationship between a cross-sectional geometry of the open channel and a contact angle defined between the open channel and the drug formulation is selected and configured such that the liquid-to-solid interfacial energy exceeds the liquid-to-vapor interfacial energy as a fluid length of the fixed volume of drug formulation is increased within the open channel.

25. The drug delivery device as in claim 24, wherein the open channel has a normalized hydraulic radius ranging from 0.1 to 0.8.

26. The drug delivery device as in claim 24, wherein the drug formulation and the cross-sectional geometry of the open channel is selected and configured such that the following constraint is satisfied:

$$\frac{d}{dL}[E_{LV} + E_{LS}]_V < 0$$

wherein, $E_{LV}$ corresponds to the liquid-to-vapor interfacial energy, $E_{LS}$ corresponds to the liquid-to-solid interfacial energy, L corresponds to the fluid length of the drug formulation and V corresponds to the fixed volume of the fluid.

27. The drug delivery device as in claim 26, wherein the open channel defines a substantially parabolic shaped cross-section.

28. The drug delivery device as in claim 26, wherein the open channel defines a substantially trapezoidal shaped cross-section.

29. The drug delivery device as in claim 1, wherein the drug formulation and the cross-sectional geometry of the open channel is selected and configured such that the open channel is self-draining.

30. The drug delivery device as in claim 11, wherein the drug formulation and the cross-sectional geometry of the open channel is selected and configured such that the open channel is self-draining.

* * * * *